US008048679B2

(12) United States Patent
DesLauriers et al.

(10) Patent No.: US 8,048,679 B2
(45) Date of Patent: Nov. 1, 2011

(54) METHOD FOR EMPLOYING SEC-FTIR DATA TO PREDICT MECHANICAL PROPERTIES OF POLYETHYLENE

(75) Inventors: Paul J. DesLauriers, Bartlesville, OK (US); David C. Rohlfing, Bartlesville, OK (US)

(73) Assignee: Chevron Phillips Chemical Company, LP, The Woodlands, TX (US)

( * ) Notice: Subject to any disclaimer, the term of this patent is extended or adjusted under 35 U.S.C. 154(b) by 0 days.

(21) Appl. No.: 12/868,552

(22) Filed: Aug. 25, 2010

(65) Prior Publication Data

US 2010/0319440 A1    Dec. 23, 2010

Related U.S. Application Data

(62) Division of application No. 11/476,339, filed on Jun. 27, 2006, now Pat. No. 7,803,629.

(51) Int. Cl.
*G01N 33/00* (2006.01)
(52) U.S. Cl. ............... 436/85; 436/86; 436/89; 436/174
(58) Field of Classification Search ............... 436/85, 436/86, 89, 174
See application file for complete search history.

(56) References Cited

U.S. PATENT DOCUMENTS

| | | |
|---|---|---|
| 4,460,750 A | 7/1984 | Thiersault et al. |
| 5,039,614 A | 8/1991 | Dekmezian et al. |
| 5,071,913 A | 12/1991 | Powers et al. |
| 5,151,474 A | 9/1992 | Lange et al. |
| 5,675,253 A | 10/1997 | Smith et al. |
| 5,700,895 A | 12/1997 | Kanda et al. |
| 6,072,576 A | 6/2000 | McDonald et al. |
| 6,506,866 B2 | 1/2003 | Jacobsen et al. |
| 6,632,680 B1 | 10/2003 | DesLauriers et al. |
| 7,056,744 B2 | 6/2006 | DesLauriers et al. |
| 7,427,506 B2 | 9/2008 | Garcia-Franco et al. |

FOREIGN PATENT DOCUMENTS

| | | |
|---|---|---|
| EP | 0341091 | 11/1989 |
| WO | WO 96/35750 | 11/1996 |
| WO | WO 98/59000 | 12/1998 |

OTHER PUBLICATIONS

Baum et al., "Tests on Fully Synthetic Hydrocarbon Waxes", Chem. Spec. Mfr. Ass'n: Producers Mid-Year Meeting, vol. 57, pp. 160-164, 1971.
Blitz, et al., "The Characterization of Short Chain Branching in Polyethylene Using Fourier Transform Infrared Spectroscopy", J. Appl. Polym. Soc., vol. 51, pp. 13-20, 1994.
DesLauriers, et al., "Modeling Tie Molecules in Polyethylene". Aug. 28, 2006.
DesLauriers, et al., "Quantifying the Effects of Polymer Microstructure on Slow Crack Growth Resistance in Polyethylene", 2006 International Polyolefins Conference—Feb. 28-Mar. 1, 2006, Houston TX.

(Continued)

*Primary Examiner* — Sam P Siefke
(74) *Attorney, Agent, or Firm* — Fletcher Yoder PC

(57) ABSTRACT

The present invention provides several methods of determining values of physical or chemical properties of polymers. In these methods, at least two polymer training samples are provided. Characteristics of the polymer microstructures of the training samples are correlated with values of physical or chemical properties of the training samples. These correlations are subsequently applied to the respective characteristics of polymer test samples in order to determine the values of physical or chemical properties of the test samples.

20 Claims, 26 Drawing Sheets

OTHER PUBLICATIONS

DesLauriers, P.J., et al., "Quantifying Short Chain Branching Microstructures in Ethylene 1-Olefin Copolymers . . . " Polymer, vol. 43, pp. 159-170, 2002.

Hanson, Charles M., "On Predicting Environmental Stress Cracking in Polymers," Polymer Degradation and Stability, vol. 77, No. 1 (2002), pp. 43-53.

http://pep.sric.sri.com/Public/Reports/Phase95/RP019F.html, "Process Economics Program Report 19", Nov. 1966.

http://wwwchem.scustan.edu/Tutorials/INFRARED.HTL, "Interpretation of Infrared Spectra", Nov. 2000.

Huang, Y.L. et al., "Dependence of Slow Crack Growth in Polyethylene on Butyl Branch Density: Morphology and Theory", Journal of Polymer Science, Part B: Polymer Physics, vol. 29, pp. 129-137, 1991.

Huang, Y.L. et al., "The Dependence of Butyl Branch Density on Slow Crack Growth in Polyethylene: Kinetics", Journal of Polymer Science, Part B: Polymer Physics, vol. 28, pp. 2007-2021, 1990.

Huang, Y.L. et al., "The Effect of Molecular Weight on Slow Crack Growth in Linear Polyehtylene Homopolymers", Journal of Materials Science, vol. 23, pp. 3648-3655, 1988.

Jordens, K. et al., "The Influence of Molecular Weight and Thermal History on the Thermal, Rheological . . . ", Polymer, vol. 41, pp. 7175-7192, 2000.

Mirabella, F.M., et al., "Determination of the Crystallinity of Polyethylene/a-Olefin Copolymers by Thermal Analysis . . . ", Journal of Polymer Science, Part B: Polymer Physics, vol. 40, pp. 1637-1643, 2002.

Nielsen, Tenna B., et al., "Surface Wetting and the Prediction of Environmental Stress Cracking (ESC) in Polymers," Polymer Degradation and Stability, vol. 89, No. 3 (2005), pp. 513-516.

Parker, et al., "Vibrational Absorption Intensities in Chemical Analysis, 9. The Near-Infrared Spectra of Methyl Branched Alkanes", J. Phys. Chem. A, vol. 101:50, pp. 9618-9631, 1997.

Patel, R.M., et al., "Theoretical Prediction of Tie-Chain Concentration and Its Characterization Using Postyield Response", J. Appl. Poly., Sci., vol. 60, pp. 749-758, 1996.

PCT International Search Report, Mailed Jan. 2, 2008, pp. 4.

Pedraza, J.J., "Probability of Formation of a Tie Molecule in Polydisperse Polyethylenes", Anales De Quimica, vol. 95, pp. 321-326, 1995.

Seguela, R., "Critical Review of the Molecular Topology of Semicrystalline Polymers . . . " Journal of Polymer Science, Part B: Polymer Physics, vol. 43, pp. 1729-1748, 2005.

Stark, "Near-Infrared Spectroscopy: The New FT Frontier-Spectroscopic and Chemometric Considerations", Proc. SPIE-Ing. Soc. Opt. Eng (1992, International Conference Fourier Transform Spectro. 8th (1991) pp. 70-86.

Tso, C.C., et al., "Comparison of Methods for Characterizing Comonomer Composition in Ethylene 1-Olefin Copolymers: 3D-TREF vs. SEC-FTIR", Polymer, vol. 45, pp. 2657-2663, 2004.

Yeh, T. et al, "Fatigue Crack Propagation in High-Density Polyethylene", Journal of Polymer Science, Part B: Polymer Physics, vol. 29, pp. 371-388, 1991.

Zhou, Z. et al, "The Effect of Blending High-Density and Linear Low-Density Polyethylenes on Slow Crack Growth", Polymer, vol. 34, pp. 2520-2523, 1993.

Log PENT (h) @ 2.4 MPa

PSP1

Density (g/mL)

Log $M_w$

BM-1

BM-2

BM-3

BM-4

BM-5

BM-6

BM-7

Log PENT (h) @ 2.4 MPa

Log PENT (h) @ 2.4 MPa ial or chemical property of at least one polymer test sample comprises:

METHOD FOR EMPLOYING SEC-FTIR DATA TO PREDICT MECHANICAL PROPERTIES OF POLYETHYLENE

CROSS-REFERENCE TO RELATED APPLICATIONS

This application is a divisional of U.S. patent application Ser. No. 11/476,339, entitled "A METHOD FOR EMPLOYING SEC-FTIR DATA TO PREDICT MECHANICAL PROPERTIES OF POLYETHYLENE" filed on Jun. 27, 2006, which is incorporated by reference herein in its entirety.

BACKGROUND OF THE INVENTION

The present invention is directed to methods of determining values of physical or chemical properties of polymers. Traditionally, in order to determine a value of a specific physical or chemical property, a certain quantity of the particular polymer resin was needed to fabricate an article or a test specimen, and then the resulting article or test specimen was subsequently tested via the prescribed analytical test procedure to determine the value of the physical or chemical property. This procedure is cumbersome not only due to the time required for fabricating the article or test specimen, but also the time required to perform the respective analytical test procedure. Further, the traditional method, depending upon the particular test, could require large amounts of polymer, often more than could be produced in small-scale research laboratory or pilot plant apparatus.

Hence, there exists a need for a method of determining a value of a desired chemical or physical property of a test sample that requires only a small amount of polymer for analysis. Further, this method should provide for the value of the physical or chemical property of the test sample to be determined without fabricating an article or a test specimen. Still further, this method should allow determination of the value of the physical or chemical property of the test sample without performing the analytical test for the physical or chemical property.

In another aspect, there is a need for a method of rapidly determining a value of a desired chemical or physical property of a test sample. It is beneficial to determine the value of the chemical or physical property without having to invest the time and expense needed to fabricate articles or test specimens for subsequent analysis, nor to invest the time and expense needed to perform the analytical test procedure, which dependent upon the specific test, could take days or weeks to determine the value of the respective property. The cycle time of resin design and product development to achieve a desired physical or chemical property attribute could be greatly reduced with a method that provided rapid feedback using only a small quantity of a polymer test sample. Accordingly, the methods of the present invention are directed above.

BRIEF SUMMARY OF THE INVENTION

The present invention discloses a method of determining values of physical or chemical properties of polymers. In one aspect, the present invention provides a method of determining a value of a physical or chemical property of at least one polymer test sample. The at least one polymer test sample has a molecular weight distribution (MWD) profile and a short chain branching distribution (SCBD). In this aspect, the method of determining a value of a physical or chemical property of the at least one polymer test sample comprises:

a) providing at least two polymer training samples, each training sample having a MWD profile, a SCBD, and a known value of the respective physical or chemical property;

b) determining at least two weighted cross terms at respective molecular weights along the MWD profile and the SCBD, for each of the at least two polymer training samples and the at least one polymer test sample, each weighted cross term being determined as the multiplication product of:

(1) the respective molecular weight;
(2) the weight fraction at the respective molecular weight; and
(3) the number of short chain branches per 1000 carbon atoms at the respective molecular weight;

c) plotting each weighted cross term versus the logarithm of the respective molecular weight for each of the at least two polymer training samples and the at least one polymer test sample;

d) determining the respective area under each curve in step c);

e) correlating the respective areas for each of the at least two polymer training samples in step d) with the known value of the respective physical or chemical property; and f) applying the correlation of step e) to the respective area of the at least one polymer test sample to determine the value of the physical or chemical property of the at least one polymer test sample.

In another aspect of the present invention, the method is directed to a single-point determination. That is, the weighted cross term is determined at a single molecular weight. In this aspect, the present invention provides a method of determining a value of a physical or chemical property of at least one polymer test sample. The at least one polymer test sample has a molecular weight, a weight fraction at the respective molecular weight, and a number of short chain branches per 1000 carton atoms at the respective molecular weight. This method comprises:

a) providing at least two polymer training samples, each training sample having a molecular weight, a weight fraction at the respective molecular weight, a number of short chain branches per 1000 carton atoms at the respective molecular weight, and a known value of the respective physical or chemical property;

b) determining a weighted cross term at the respective molecular weight for each of the at least two polymer training samples and the at least one polymer test sample, each weighted cross term being determined as the multiplication product of:

(1) the respective molecular weight;
(2) the weight fraction at the respective molecular weight; and
(3) the number of short chain branches per 1000 carbon atoms at the respective molecular weight;

c) correlating the respective weighted cross terms for each of the at least two polymer training samples in step b) with the known value of the respective physical or chemical property; and d) applying the correlation of step c) to the weighted cross term of the at least one polymer test sample to determine the value of the physical or chemical property of the at least one polymer test sample.

In yet another aspect of the present invention, a chemometric method can be used to determine a value of a physical or chemical property of at least one polymer test sample. The at least one polymer test sample has a MWD profile and a SCBD. This method comprises:

a) providing at least two polymer training samples, each training sample having a MWD profile, a SCBD, and a known value of the respective physical or chemical property;

b) determining at least two weighted cross terms at respective molecular weights along the MWD profile and the SCBD, for each of the at least two polymer training samples and the at least one polymer test sample, each weighted cross term being determined as the multiplication product of:
(1) the respective molecular weight;
(2) the weight fraction at the respective molecular weight; and
(3) the number of short chain branches per 1000 carbon atoms at the respective molecular weight;

c) by chemometric analysis, defining a mathematical relationship between the values of the respective physical or chemical property and the weighted cross terms for each of the at least two polymer training samples; and d) applying the mathematical relationship of step c) to the respective weighted cross terms of step b) for the at least one polymer test sample to determine the value of the physical or chemical property of the at the least one polymer test sample.

In a different aspect, the present invention provides a method of determining a value of a physical or chemical property of at least one polymer test sample using tie molecule probabilities. For example, the at least one polymer test sample has a composite density, a MWD profile, and a SCBD. The method of determining a value of a physical or chemical property of the at least one polymer test sample comprises:

a) providing at least two polymer training samples, each training sample having a composite density, a MWD profile, a SCBD, and a known value of the respective physical or chemical property;

b) determining at least two density terms at respective molecular weights along the MWD profile and the SCBD, for each of the at least two polymer training samples and the at least one polymer test sample, each density term being determined using the composite density, the MWD profile, and the SCBD;

c) determining a respective melting temperature from each density term in step b);

d) determining a respective probability for tie molecule formation from each melting temperature in step c);

e) determining a respective weighted tie molecule probability, each weighted tie molecule probability being determined as the multiplication product of:
(1) the weight fraction at the respective molecular weight; and
(2) the probability for tie molecule formation in step d) at the respective molecular weight;

f) plotting each weighted tie molecule probability versus the logarithm of the respective molecular weight for each of the at least two polymer training samples and the at least one polymer test sample;

g) determining the respective area under each curve in step f);

h) correlating the respective areas for each of the at least two polymer training samples in step g) with the known value of the respective physical or chemical property; and i) applying the correlation of step h) to the respective area of the at least one polymer test sample to determine the value of the physical or chemical property of the at least one polymer test sample.

A further aspect of the present invention is a single-point method which utilizes tie molecule probabilities. That is, the weighted tie molecule probability is determined at a single molecular weight. In this aspect, the present invention provides a method of determining a value of a physical or chemical property of at least one polymer test sample. The at least one polymer test sample has a composite density, a molecular weight, and a weight fraction at the respective molecular weight. This method comprises:

a) providing at least two polymer training samples, each training sample having a composite density, a molecular weight, a weight fraction at the respective molecular weight, and a known value of the respective physical or chemical property;

b) determining a minimum molecule length for a tie molecule ($2L_c+L_a$) using the composite density for each of the at least two polymer training samples and the at least one polymer test sample;

c) determining a respective probability for tie molecule formation at the respective molecular weight from each $2L_c+L_a$ of step b);

d) determining a respective weighted tie molecule probability, each weighted tie molecule probability being determined as the multiplication product of:
(1) the weight fraction at the respective molecular weight; and
(2) the probability for tie molecule formation in step c) at the respective molecular weight;

e) correlating the respective weighted tie molecule probability for each of the at least two polymer training samples in step d) with the known value of the respective physical or chemical property; and f) applying the correlation of step e) to the weighted tie molecule probability of the at least one polymer test sample to determine the value of the physical or chemical property of the at least one polymer test sample.

DEFINITIONS

The following definitions are provided in order to aid those skilled in the art in understanding the detailed description of the present invention.

dW/d Log M—Weight fraction.
ESCR—Environmental Stress Crack Resistance, ASTM D1693.
FNCT—Full Notched Creep Test, ISO 16770.
FTIR—Fourier Transform-Infrared spectrophotometry.
M or MW—Molecular weight.
MWD—Molecular weight distribution.
$M_n$—Number average MW.
$M_w$—Weight average MW.
NDR—Natural Draw Ratio, ASTM D638.
NPT—Notched Pipe Test, ISO 13479.
PENT—Pennsylvania Notched Test, ASTM F1473, measured in hours.
PSP1—Primary structure parameter 1; calculated by dividing the area under the curve of the plot of the weighted cross term versus molecular weight by 100,000.
PSP2—Primary structure parameter 2; calculated by multiplying the area under the curve of the plot of the weighted tie molecule probability versus molecular weight by 100.
$P_{TM}$ or P—Probability for tie molecule formation.
SCBD—Short chain branching distribution.
SCB's—Number of short chain branches per 1000 carbon atoms.
SEC—Size Exclusion Chromatography; also referred to as Gel Permeation Chromatography (GPC).
SP-NCTL—Single Point Notched Constant Tensile Load, ASTM D5397, 30% yield.
Weighted cross term—Multiplication product of a molecular weight, the weight fraction at the respective molecular weight, and the number of short chain branches per 1000 carbon atoms at the respective molecular weight; also shown as M*dW/d(Log M)*SCB.

Weighted tie molecule probability—Multiplication product of the weight fraction at a molecular weight and the probability for tie molecule formation at the respective molecular weight; also shown as dW/d(Log M)*$P_{TM}$.

$2L_c+L_a$—Minimum molecule length for a tie molecule; $L_c$ is the crystalline lamella thickness and $L_a$ is the amorphous layer thickness.

DETAILED DESCRIPTION OF THE INVENTION

Figure 1:
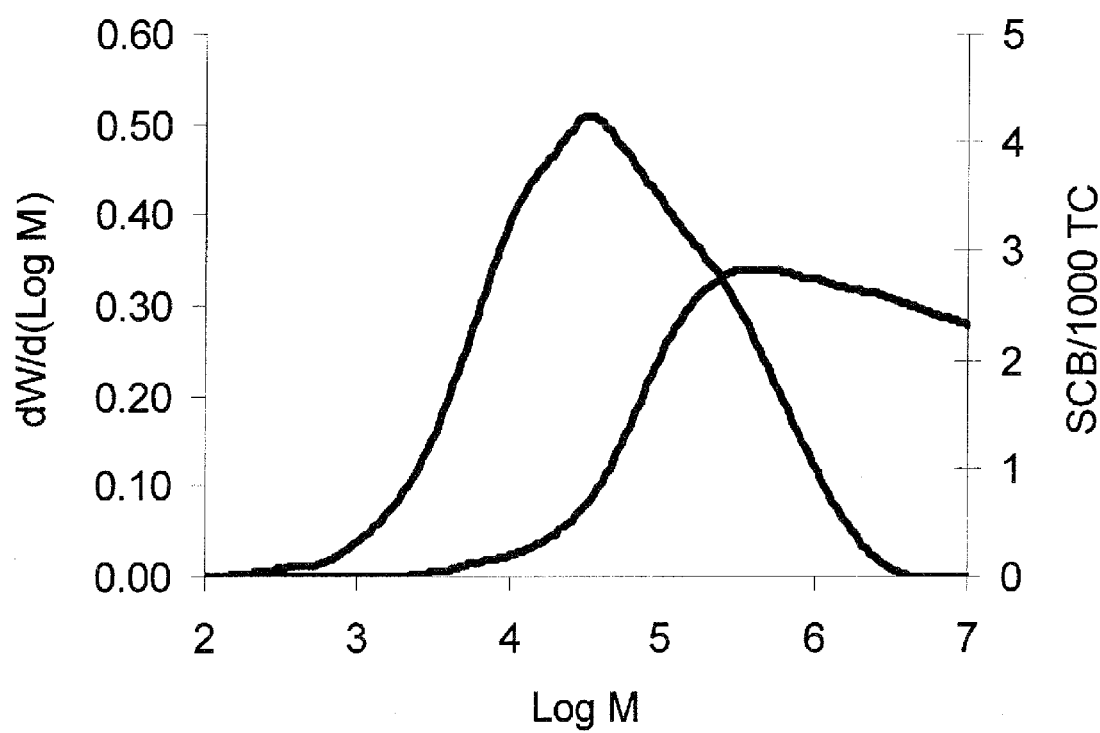
FIG. 1 presents a plot of the molecular weight distribution (MWD) profile and the short chain branching distribution (SCBD) for an exemplary polyolefin copolymer.

The present invention is directed to a method of determining values of physical or chemical properties of polymers. Exemplary physical or chemical properties of interest in the present invention include, but are not limited to, PENT, ESCR, SP-NCTL, NPT, FNCT, NDR, izod impact, dart impact, Charpy impact, puncture resistance, or Elmendorf tear strength. The PENT value can be determined at different conditions, such as, for example, 2.4 MPa, 3.0 MPa, or 3.8 MPa.

The method of the present invention is applicable to all classes of polymers, although the method is particularly well suited for semi-crystalline polymers. The invention will be described in connection with polyolefins, particularly polyethylene homopolymers and copolymers. It is understood that the present invention is not limited to the aspects and examples outlined herein, and that the present invention includes all alternatives, modifications, and equivalents as may be included within the spirit and the scope of the specification and claims that follow.

Differences in the polymer microstructure, such as the MWD profile and the SCBD of a given polymer, can influence the resulting physical or chemical properties of that polymer. Thus, in one aspect of the present invention, the method described herein can determine the values of physical or chemical properties of test samples using knowledge of the respective test samples MWD profile and SCBD. In another aspect, a method in accordance with this invention further requires a composite resin density of the polymer test sample.

The MWD profile of a polymer can be provided by any means known to one or ordinary skill in the art. A non-limiting example of an analytical technique to determine the MWD profile of a polymer is SEC or GPC. Inherently, as used in this disclosure, the MWD profile of a polymer can provide, among other data, the MWD data and associated weight fraction at each MW, including common terms useful in the art such as $M_w$ and $M_n$.

Similarly, the SCBD of a polymer can be provided by any means known to one of skill in the art. Techniques could include, but are not limited to, temperature rising elution fractionation (TREF), nuclear magnetic resonance (NMR), and SEC-FTIR. Inherently, as used in this disclosure, the SCBD of a polymer can provide the number of short chain branches per 1000 carbon atoms (SCB's) at each MW across the MWD profile.

One method to provide both the MWD profile and the SCBD of a polymer is SEC-FTIR using chemometric analysis, described in U.S. Pat. No. 6,632,680 and U.S. patent application Ser. No. 10/463,849, the disclosures of which are incorporated in their entirety by this reference. An advantage of SEC-FTIR as it relates to the methods of the present invention is the small quantity of the polymer training samples and of the polymer test samples that are required for analysis to determine the MWD profile and the SCBD. In one aspect of the present invention, less than about 5 grams each of the respective test or training samples is provided for determination of the MWD profile and the SCBD. In another aspect, less than about 1 gram is provided for analysis. In a further aspect, less than about 100 milligrams is provided. Further, another advantage of the present invention is the quick determination of a physical or chemical property of a test sample as compared to conventional testing and measurement methods. Using a technique such as SEC-FTIR in combination with the methods of the present invention, the value of a physical or chemical property can be determined in less than three hours. In another aspect, the value of a physical or chemical property can be determined in less than two hours. In yet another aspect, the value of a physical or chemical property can be determined in less than one hour.

Composite resin density likewise can be determined by any means known to one of ordinary skill in the art. Analytical techniques include, but are not limited to, refractive index or molded density per ASTM D 1238. The composite resin density is the density of the polymer as a whole, across all molecular weights.

While methods are described in terms of "comprising" various steps, the methods can also "consist essentially of" or "consist of" the various steps.

Primary Structure Parameter 1 (PSP1)

One aspect of the present invention provides a method of determining a value of a physical or chemical property of at least one polymer test sample, the at least one polymer test sample having a molecular weight distribution (MWD) profile and a short chain branching distribution (SCBD). The MWD profile and the SCBD can be determined via any analytical technique known to one of ordinary skill in the art, such as SEC-FTIR. The polymer test sample can also be referred to as an experimental sample or an unknown sample. The method of determining a value of a physical or chemical property of the at least one polymer test sample comprises:

a) providing at least two polymer training samples, each training sample having a MWD profile, a SCBD, and a known value of the respective physical or chemical property;

b) determining at least two weighted cross terms at respective molecular weights along the MWD profile and the SCBD, for each of the at least two polymer training samples and the at least one polymer test sample, each weighted cross term being determined as the multiplication product of:
  (1) the respective molecular weight;
  (2) the weight fraction at the respective molecular weight; and
  (3) the number of short chain branches per 1000 carbon atoms at the respective molecular weight;

c) plotting each weighted cross term versus the logarithm of the respective molecular weight for each of the at least two polymer training samples and the at least one polymer test sample;

d) determining the respective area under each curve in step c);

e) correlating the respective areas for each of the at least two polymer training samples in step d) with the known value of the respective physical or chemical property; and f) applying the correlation of step e) to the respective area of the at least one polymer test sample to determine the value of the physical or chemical property of the at least one polymer test sample.

At least two different polymer training samples are provided in accordance with the methods of the present invention. Training samples can also be referred to as control samples. Each polymer training sample has a known MWD profile and a known SCBD. The MWD profile and the SCBD can be determined using a technique such as SEC-FTIR, as mentioned above. For an exemplary polyolefin copolymer, FIG. 1 illustrates the MWD profile and the SCBD of the copolymer. The x-axis is the logarithm of the molecular weight, the left hand side y-axis is the weight fraction at each molecular weight, and the right hand side y-axis is the number of short chain branches per 1000 carbon atoms (SCB's). Graphical data as illustrated in FIG. 1 can be provided for both the at least two polymer training samples and the at least one polymer test sample.

Further, each polymer training sample has a known value of the respective physical or chemical property that is of interest. For instance, at least two polymer training samples can be provided that each have a known value of PENT at 2.4 MPa, the PENT value having been determined previously using the respective analytical test for PENT.

At least two polymer training samples are used in the methods of the present invention. Alternatively, however, at least three training samples, at least four training samples, at least five training samples, at least ten training samples, at least fifteen training samples, or at least twenty training samples, can be used. There is no specific upper limit on the number of different training samples that can be used with the present invention. It is beneficial that the training samples resemble the polymer test sample, and that the range covered by the training samples encompass the polymer test sample, but this is not required. Further, the training samples can include duplicate or redundant samples to include the impact of experimental error in the tests for MWD profile and SCBD, and of the respective physical or chemical property of interest.

For each of the at least two polymer training samples and the at least one polymer test sample, weighted cross terms can be determined using the respective data for each sample as exemplified in FIG. 1. A weighted cross term is the multiplication product of a molecular weight, the weight fraction at the respective molecular weight, and the number of short chain branches per 1000 carbon atoms at the respective molecular weight (i.e., M*dW/d(Log M)*SCB's). While not intending to be bound by this theory, Applicants submit that one factor related to polymers with improved toughness (e.g., tear, impact, puncture, or stress crack resistance) is the presence of more short chain branching at higher molecular weights. That is, the presence of high levels of branching at lower molecular weights does not contribute significantly to improved toughness (e.g., in properties such as PENT, SP-NCTL, dart impact, and the like). Rather, high short chain branch content present on the high molecular weight end of the MWD profile can contribute significantly to improved toughness of polymers. Again, not intending to be bound by this theory, Applicants believe that the weighted cross term, as defined above, captures the impact of having a higher branching content on the higher molecular weight fraction of the polymer.

Figure 2:
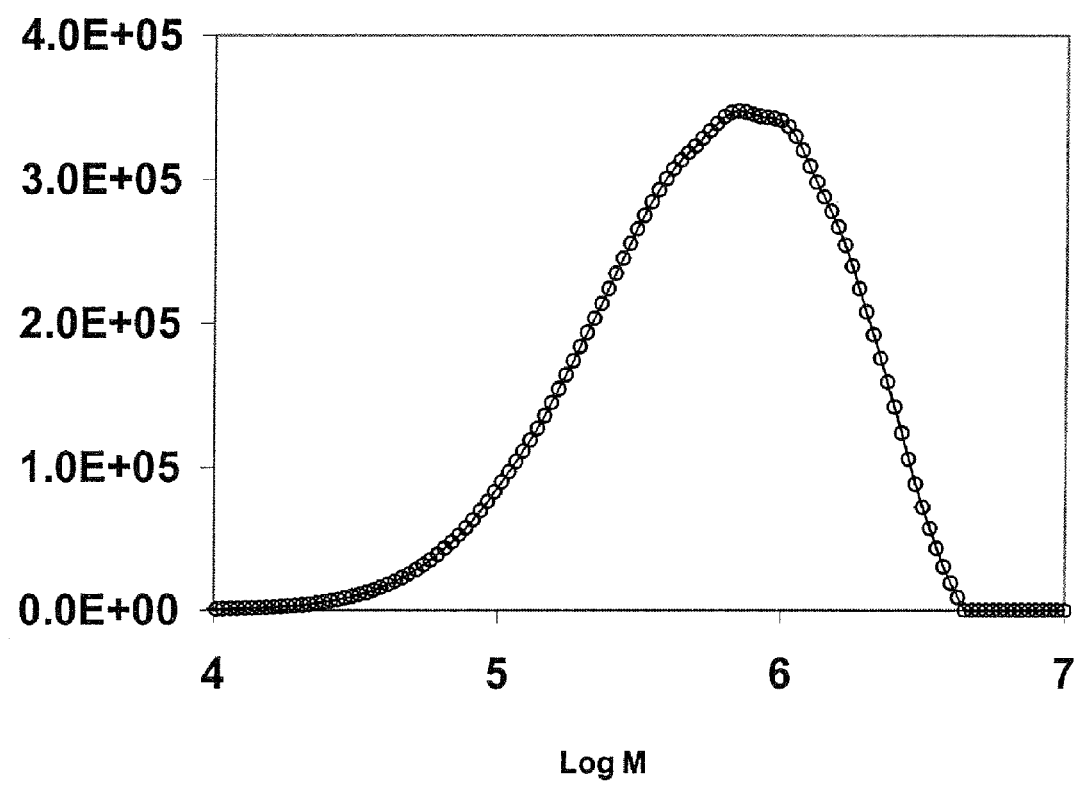
FIG. 2 presents a plot of the weighted cross term versus the logarithm of the molecular weight for an exemplary polyolefin copolymer.

In accordance with one aspect of the present invention, at least two weighted cross terms at respective molecular weights along the MWD profile and the SCBD are required. Each weighted cross term is plotted versus the logarithm of the respective molecular weight, for each of the at least two polymer training samples and the at least one polymer test sample. This is illustrated in FIG. 2 for an exemplary polyolefin copolymer. Although at least two weighted cross terms are required, it is beneficial to have many more cross terms across the range of molecular weights to form a curve as illustrated in FIG. 2. Hence, in accordance with another aspect of the present invention, at least five weighted cross terms, at least ten weighted cross terms, at least twenty-five weighted cross terms, at least fifty weighted cross terms, or at least one hundred weighted cross terms, can be used. There is no specific upper limit on the number of weighted cross terms that can be used with the present invention. More weighted cross terms provide a smoother curve as illustrated in FIG. 2.

Figure 3:
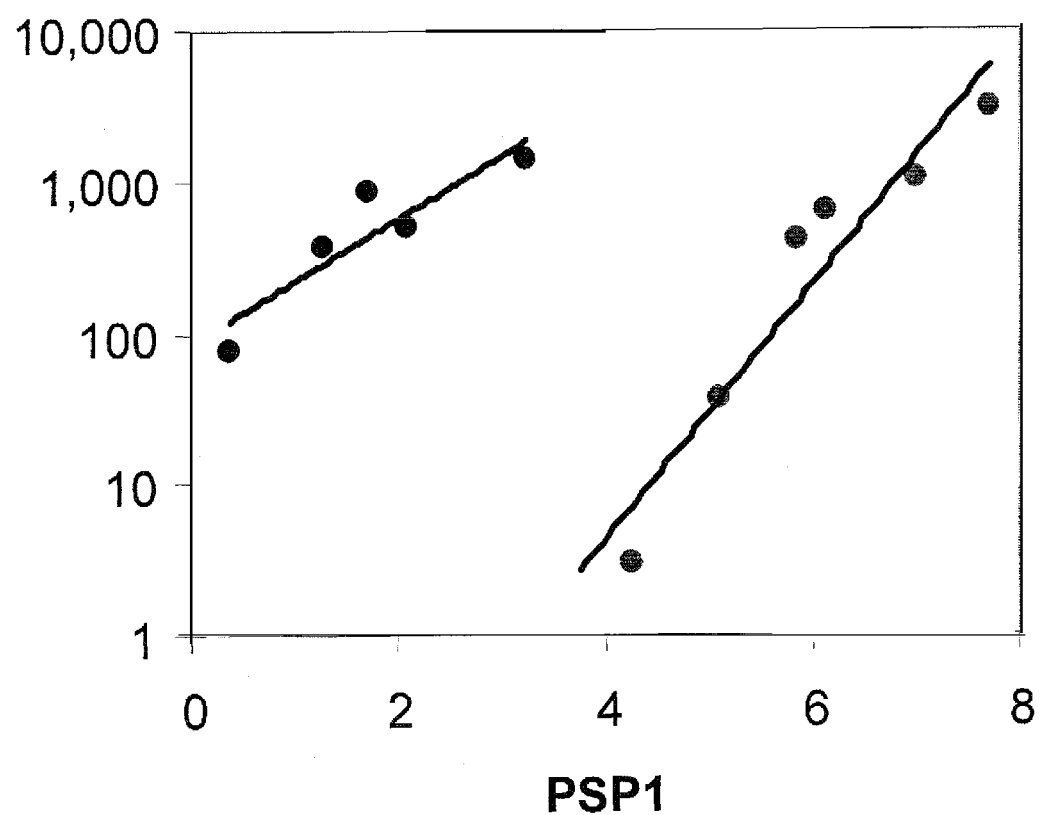
FIG. 3 presents a plot of Log PENT (in hours) at 2.4 MPa versus primary structure parameter 1 (PSP1) for two exemplary series of polyolefin polymers.

For each of the at least two polymer training samples and the at least one polymer test sample, the area under the respective curve for each sample is determined For example, the area under the curve in FIG. 2 for the exemplary copolymer is determined. The respective areas under the curve for each of the at least two polymer training samples are then correlated with the respective value of the physical or chemical property or properties of interest. In one aspect of the present invention, the area under each curve is divided by 100,000 to calculate primary structure parameter 1 (PSP1). FIG. 3 illustrates a correlation of a specific physical or chemical property (in this case, Log PENT at 2.4 MPa) versus PSP1 for two exemplary series of polyolefin polymers. The results indicate that there is a linear relationship between the logarithm of the property of interest and the PSP1 value, which is impacted by the branch content of the high molecular weight fraction of the copolymer.

By applying a correlation, such as illustrated in FIG. 3, to the respective area under the curve of the at least one polymer test sample, the value of the physical or chemical property of interest for the at least one polymer test sample can be determined This method is further illustrated in Examples 1-2 that follow.

Another aspect of the present invention provides a method of determining a value of a physical or chemical property of at least one polymer test sample, the at least one polymer test sample having a molecular weight, a weight fraction at the respective molecular weight, and a number of short chain branches per 1000 carton atoms at the respective molecular weight. These parameters can be determined from a MWD profile and a SCBD via any analytical technique known to one of ordinary skill in the art, such as SEC-FTIR. This method of determining a value of a physical or chemical property of the at least one polymer test sample comprises:

a) providing at least two polymer training samples, each training sample having a molecular weight, a weight fraction at the respective molecular weight, a number of short chain branches per 1000 carton atoms at the respective molecular weight, and a known value of the respective physical or chemical property;

b) determining a weighted cross term at the respective molecular weight for each of the at least two polymer training samples and the at least one polymer test sample, each weighted cross term being determined as the multiplication product of:
(1) the respective molecular weight;
(2) the weight fraction at the respective molecular weight; and
(3) the number of short chain branches per 1000 carbon atoms at the respective molecular weight;

c) correlating the respective weighted cross terms for each of the at least two polymer training samples in step b) with the known value of the respective physical or chemical property; and d) applying the correlation of step c) to the weighted cross term of the at least one polymer test sample to determine the value of the physical or chemical property of the at least one polymer test sample.

The above method is a single-point determination of the method illustrated in FIGS. 1-3. In this method, a single weighted cross term at a single molecular weight is determined for each of the at least two polymer training samples and the at least one polymer test sample. This method is further illustrated by Example 3 that follows.

It is apparent from FIG. 3 that not all polymer types have the same correlation between the physical or chemical property and the weighted cross term or PSP1. For instance, each family of polyolefin resins produced with different catalyst systems (such as chromium, Ziegler-Natta, metallocene, and the like, or combinations thereof) or with different production processes (such as slurry, solution, gas phase, and the like, or combinations thereof) may have a different calibration curve, or a different relationship with the physical or chemical property of interest.

In accordance with a further aspect of the present invention, a chemometric method can be used to determine a value of a physical or chemical property of at least one polymer test sample, the at least one polymer test sample having a MWD profile and a SCBD. This method comprises:

a) providing at least two polymer training samples, each training sample having a MWD profile, a SCBD, and a known value of the respective physical or chemical property;

b) determining at least two weighted cross terms at respective molecular weights along the MWD profile and the SCBD, for each of the at least two polymer training samples and the at least one polymer test sample, each weighted cross term being determined as the multiplication product of:
(1) the respective molecular weight;
(2) the weight fraction at the respective molecular weight; and
(3) the number of short chain branches per 1000 carbon atoms at the respective molecular weight;

c) by chemometric analysis, defining a mathematical relationship between the values of the respective physical or chemical property and the weighted cross terms for each of the at least two polymer training samples; and d) applying the mathematical relationship of step c) to the respective weighted cross terms of step b) for the at least one polymer test sample to determine the value of the physical or chemical property of the at the least one polymer test sample.

This chemometric method can be used when the at least two polymer training samples and the at least one polymer test sample are prepared using catalyst systems that are the same or are different. For example, this method can be used for different families of polyolefin resins produced with different catalyst systems (such as chromium, Ziegler-Natta, metallocene, and the like, or combinations thereof) or with different production processes (such as slurry, solution, gas phase, and the like, or combinations thereof).

Chemometric analysis was described also in U.S. Pat. No. 6,632,680 and U.S. patent application Ser. No. 10/463,849. In the present invention, chemometric analysis can be used to define a mathematical relationship between the values of the respective physical or chemical properties and the weighted cross terms for each of the at least two polymer training samples. At least two polymer training samples are used in this aspect of the present invention. Alternatively, however, at least three training samples, at least four training samples, at least five training samples, at least ten training samples, at least fifteen training samples, or at least twenty training samples, can be used. There is no specific upper limit on the number of different training samples that can be used in this aspect of the present invention. This chemometric method is further illustrated by Examples 4-5 that follow.

Primary Structure Parameter 2 (PSP2)

In another aspect, the present invention provides a method of determining a value of a physical or chemical property of at least one polymer test sample, the at least one polymer test sample having a composite density, a MWD profile, and a SCBD. The composite density can be determined via any analytical technique known to one of ordinary skill in the art, as mentioned above. The method of determining a value of a physical or chemical property of the at least one polymer test sample comprises:

a) providing at least two polymer training samples, each training sample having a composite density, a MWD profile, a SCBD, and a known value of the respective physical or chemical property;

b) determining at least two density terms at respective molecular weights along the MWD profile and the SCBD, for each of the at least two polymer training samples and the at least one polymer test sample, each density term being determined using the composite density, the MWD profile, and the SCBD;

c) determining a respective melting temperature from each density term in step b);

d) determining a respective probability for tie molecule formation from each melting temperature in step c);

e) determining a respective weighted tie molecule probability, each weighted tie molecule probability being determined as the multiplication product of:

(1) the weight fraction at the respective molecular weight; and (2) the probability for tie molecule formation in step d) at the respective molecular weight;

f) plotting each weighted tie molecule probability versus the logarithm of the respective molecular weight for each of the at least two polymer training samples and the at least one polymer test sample;

g) determining the respective area under each curve in step f);

h) correlating the respective areas for each of the at least two polymer training samples in step g) with the known value of the respective physical or chemical property; and i) applying the correlation of step h) to the respective area of the at least one polymer test sample to determine the value of the physical or chemical property of the at least one polymer test sample.

While not intending to be bound by this theory, Applicants believe that having more branching on the longer chains—the higher molecular weight fraction—forces these chains into the amorphous region of the polymer and thus increases the probability that they will act as tie molecules, holding the semi-crystalline polymer matrix together. These tie molecules can contribute significantly to improved toughness properties (e.g., tear, impact, puncture, or stress crack resistance) of polymers. In this aspect of the present invention, the above method is directed toward determining the value of a physical or chemical property of a polymer test sample using tie molecule probabilities.

This method of the present invention employs at least two different polymer training samples. Each polymer training sample has a known composite density, a known MWD profile, and a known SCBD. As noted previously, the composite density can be determined via ASTM D 1238, while the MWD profile and the SCBD can be determined using SEC-FTIR, for example. For an exemplary polyolefin copolymer, FIG. 1 illustrates the MWD profile and the SCBD of the copolymer. Graphical data as illustrated in FIG. 1 can be provided for both the at least two polymer training samples and the at least one polymer test sample. Further, each polymer training sample has a known value of the respective physical or chemical property that is of interest. For instance, at least two polymer training samples can be provided that each have a known value of PENT at 2.4 MPa, the PENT value having been determined previously using the respective analytical test for PENT.

At least two polymer training samples are used in the methods of the present invention. Alternatively, however, at least three training samples, at least four training samples, at least five training samples, at least ten training samples, at least fifteen training samples, or at least twenty training samples, can be used. There is no specific upper limit on the number of different training samples that can be used with the present invention. It is beneficial that the training samples resemble the polymer test sample, and that the range covered by the training samples encompass the polymer test sample, but this is not required. Further, the training samples can include duplicate or redundant samples to include the impact of experimental error in the tests for composite density, MWD profile, and SCBD, and of the respective physical or chemical property of interest.

For each of the at least two polymer training samples and the at least one polymer test sample, at least two density terms at respective molecular weights along the MWD profile and the SCBD are determined using the composite density, the MWD profile, and the SCBD. In order to determine the at least two density terms, a relationship between density and molecular weight is utilized.

Figure 4:
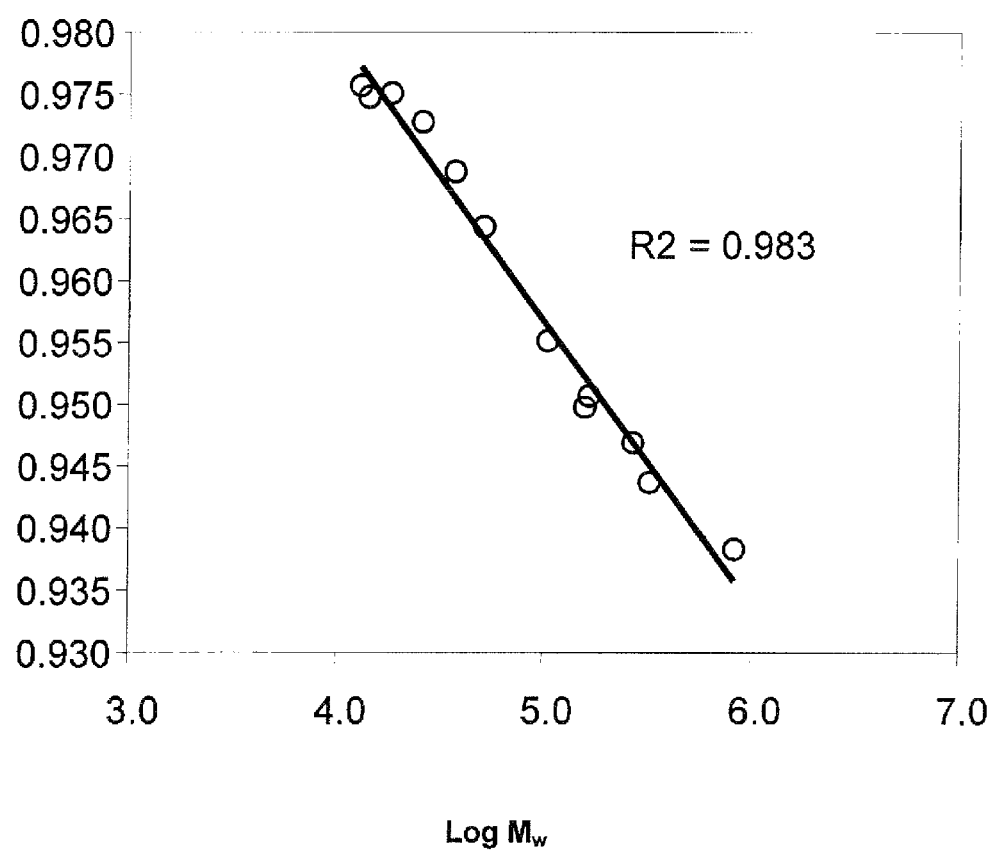
FIG. 4 presents a plot illustrating an empirical correlation of composite density versus the logarithm of weight-averaged molecular weight for an exemplary homopolymer.

The composite density of a polymer can depend on, among other things, the MWD profile and the SCBD of the polymer. In one aspect of the present invention, each density term is determined using an empirical correlation between composite density and molecular weight. For certain homopolymers such as, for example, high density polyethylene, the composite density decreases as the molecular weight increases. Using a set of narrow MWD homopolymers (polydispersity index of about 2.3) as disclosed in Jordens et al. in POLYMER, 41 (2000), 7175, an empirical correlation between composite density and molecular weight can be determined FIG. 4 illustrates a plot of composite density versus the logarithm of the weight-average molecular weight for an exemplary homopolymer, high density polyethylene. By applying this linear correlation between composite density and the logarithm of molecular weight to the exemplary MWD profile illustrated in FIG. 1, density terms at respective molecular weights can be determined.

Figure 5:
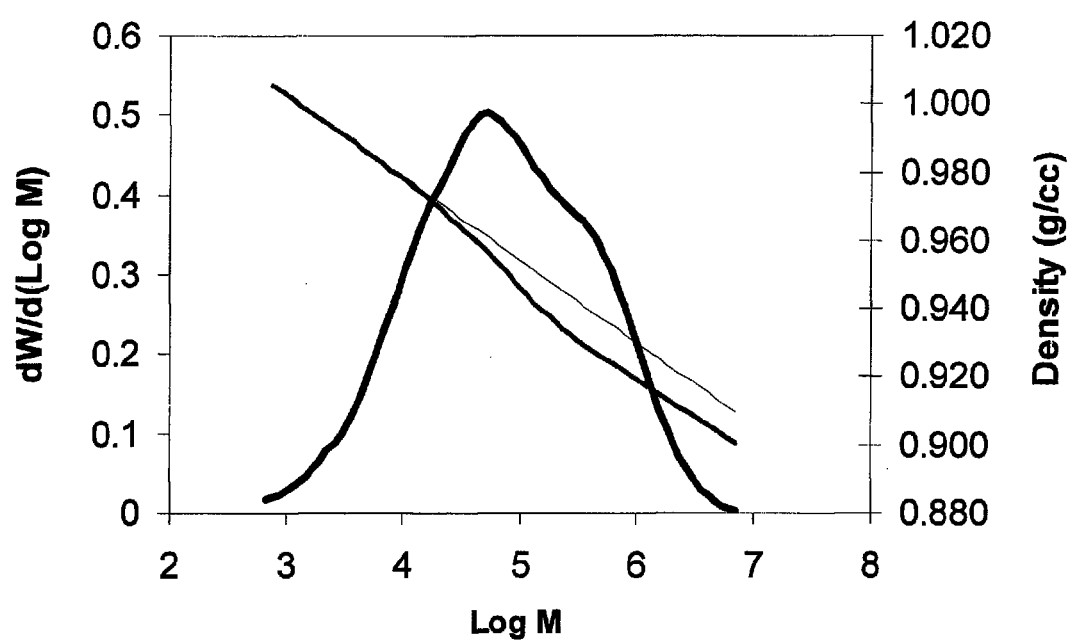
FIG. 5 presents a plot of the MWD profile and the respective homopolymer and copolymer density terms across the MWD profile for an exemplary polyolefin copolymer.

For copolymers with short chain branches or side chains which can further suppress density, a correction can be applied to the correlation of FIG. 4. The density terms derived from FIG. 4 are added based on their respective weight fraction to estimate a calculated density assuming no short chain branches. For example, assuming a copolymer with a composite density of about 0.951 g/mL, the calculated density assuming no short chain branches can be about 0.957 g/mL, a difference of about 0.006 g/mL. A correction factor based on this change in the composite density divided by the average number of SCB's in the SCBD can then be applied to determine each density term for a copolymer The average number of SCB's can be determined using analytical techniques such as NMR or SEC-FTIR. For the exemplary copolymer in FIG. 1, the average number of SCB's across the whole polymer is about 1.5. Thus, on average, the density term at each molecular weight for this exemplary copolymer decreases about 0.004 g/mL (0.006 divided by 1.5) for each short chain branch per 1000 carbon atoms. For simplicity, this assumes, although not correct, that each short chain branch suppresses density equally at all levels of SCB's and at all molecular weights across the MWD profile. This process is illustrated in FIG. 5 for the MWD profile of FIG. 1. The top line overlaying the MWD profile in FIG. 5 uses the density correlation of FIG. 4, and assumes homopolymer, i.e., no short chain branches. The lower line uses the correction factor based on the change in composite density divided by the average number of SCB's in the SCBD to determine density terms across the MWD profile for the copolymer. From FIG. 5, a copolymer density term at each respective MW can be determined.

In accordance with one aspect of the present invention, at least two density terms at respective molecular weights along the MWD profile and the SCBD are required. Although at least density two terms are required, it is beneficial to have many more density terms across the range of molecular weights to form the curves and correlations illustrated in FIG. 5. Hence, in accordance with another aspect of the present invention, at least five density terms, at least ten density terms, at least twenty-five density terms, at least fifty density terms, or at least one hundred density terms, can be used. There is no specific upper limit on the number of density terms that can be used with the present invention. More density terms can provide a more accurate correction factor and a more accurate copolymer density curve as illustrated in FIG. 5.

Figure 6:
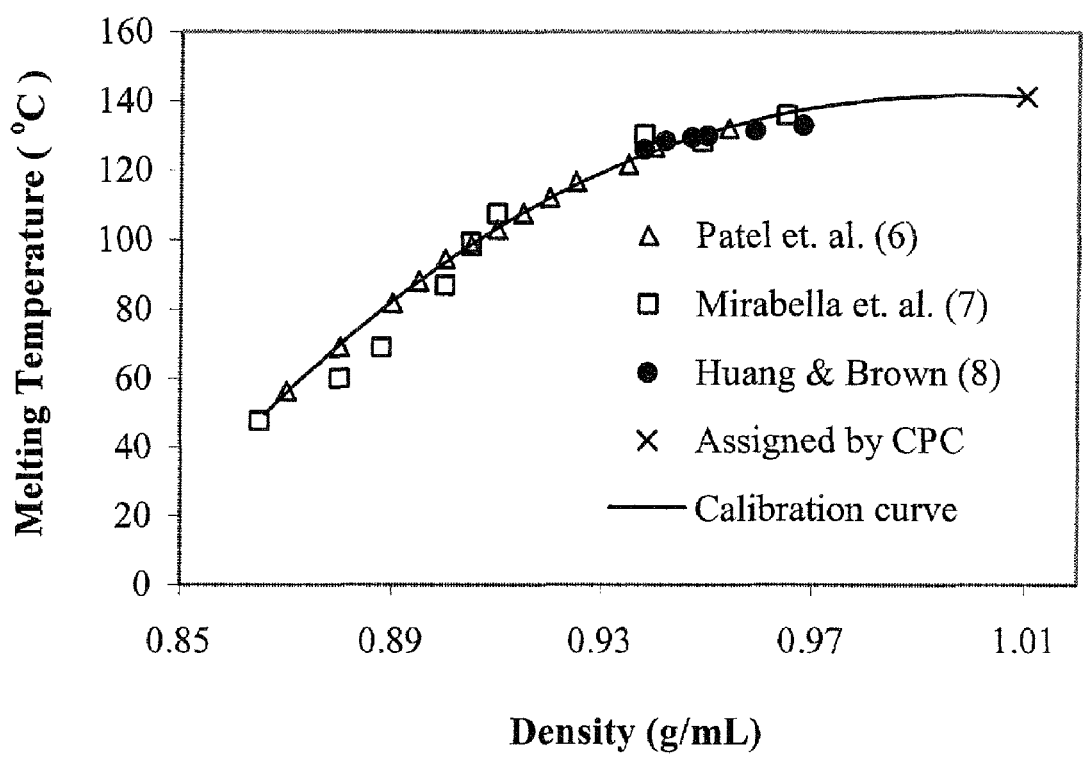
FIG. 6 presents a plot illustrating an empirical correlation of melting temperature versus density for polyethylene polymers.

A respective melting temperature can then be determined from each density term. One such method is the use of an empirical correlation between melting temperature and density, such as that illustrated in FIG. 6 for a polyethylene polymer. The data in this plot is from Patel et al. in J. APPL. POLY. SCI, 60 (1996), 749; Mirabella et al. in J. POLY. SCI., PART B: POLYMER PHYSICS, 40 (2002), 1637; and Huang et al. in J. POLY. SCI., PART B: POLYMER PHYSICS, 28 (1990), 2007. For curve fitting purposes, a point at a density of 1.01 g/mL was assigned by the Applicants. Using FIG. 6, a respective melting temperature can be determined from each density term at a respective molecular weight across the MWD profile of FIG. 5.

Figure 7:
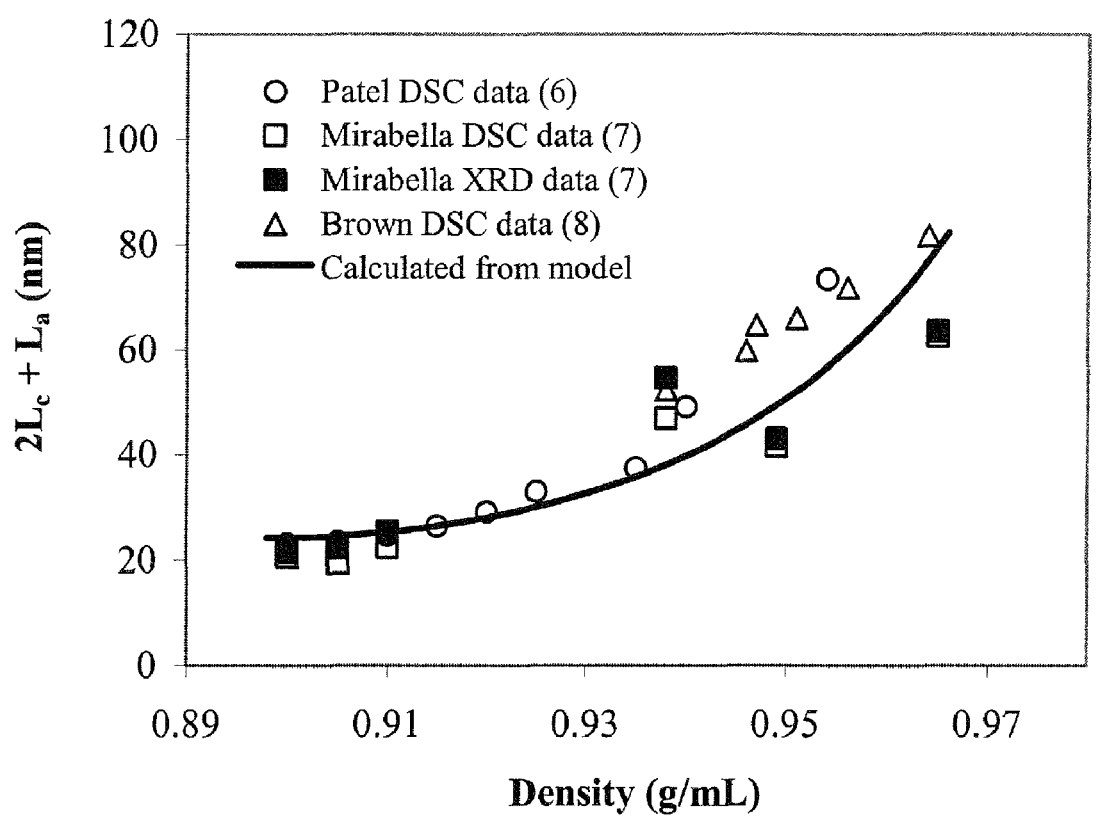
FIG. 7 presents a plot of $2L_c+L_a$ (measured in nm) as a function of density for one aspect of a method of the present invention compared with reported literature values.

In one aspect of the present invention, from each melting temperature is determined a respective probability for tie molecule formation. One technique involves determining, at each respective MW, the crystalline lamella thickness ($L_c$) and the amorphous layer thickness ($L_a$) using the melting temperature in FIG. 6 and the Gibbs-Thompson equation, which is readily known to one or ordinary skill in the art. The objective is not solely to determine $L_c$ and $L_a$, rather to determine $2L_c+L_a$ at each respective MW. $2L_c+L_a$ is generally understood to be the minimum molecule length for a tie molecule, wherein the tie molecule spans the amorphous layer and spans two crystalline lamella. FIG. 7 illustrates that the method of the present invention to determine $2L_c+L_a$ (measured in nm) as a function of density fits reasonably well with values of $2L_c+L_a$ reported by in the literature from Patel et al., Mirabella et al., and Huang et al. Some deviation of the model's prediction can be due to fact that the reported values are at a molecular weight equal to $M_w$.

Since $2L_c+L_a$ have been determined at each respective MW, the probability for tie molecule formation can be determined (abbreviated as P or $P_{TM}$). At each respective MW, $P_{TM}$ is the probability that a molecule will span a distance greater than $2L_c+L_a$ at that respective MW. Huang et al., in J. MATERIAL SCI., 23 (1988), 3648, described a method to calculate the probability of a molecule with a particular molecular weight ($M_w$) to form a tie molecule by traversing a distance $2L_c+L_a$, using the following equation:

$$P = \frac{1}{3} \frac{\int_L^\infty r^2 \exp(-b^2 r^2)\,dr}{\int_0^\infty r^2 \exp(-b^2 r^2)\,dr}$$

where $$b^2 = \frac{3}{2\bar{r}^2} \text{ and } \bar{r}^2 = (Dnl^2).$$

The symbols above have the following meanings:
P=Probability of tie-chain formation
L=Critical distance=$2L_c+L_a$
$L_c$=Lamella thickness
$L_a$=Amorphous layer thickness
D=Chain extension factor in melt=6.8 for polyethylene
n=Number of links=$M_w/14$ for polyethylene
l=The link length=0.153 nm for polyethylene.

Spreadsheet and/or computer based methods can be used to determine the value of P or $P_{TM}$ at each respective MW from the respective melting temperature. Calculated values of $P_{TM}$ using the present method compare well with values reported in the literature, such as by Patel et al. Some limitations of this method for determining $P_{TM}$ can include that $P_{TM}$ alone does not reflect the actual tie-molecule concentration in semi-crystalline polymers (i.e. loops from entanglements may serve as junction points as well). Moreover, only static tie molecule levels are accounted for in these calculations and do not include new tie chains (dynamic) that can form due to lamellar sliding as a result of deformation.

For each of the at least two polymer training samples and the at least one polymer test sample, weighted tie molecule probabilities can be determined using the respective data for each sample. A weighted tie molecule probability is the multiplication product of a weight fraction at a respective molecular weight and $P_{TM}$, the probability for tie molecule formation, at the respective molecular weight (i.e., dW/d(Log M)*$P_{TM}$).

Figure 8:
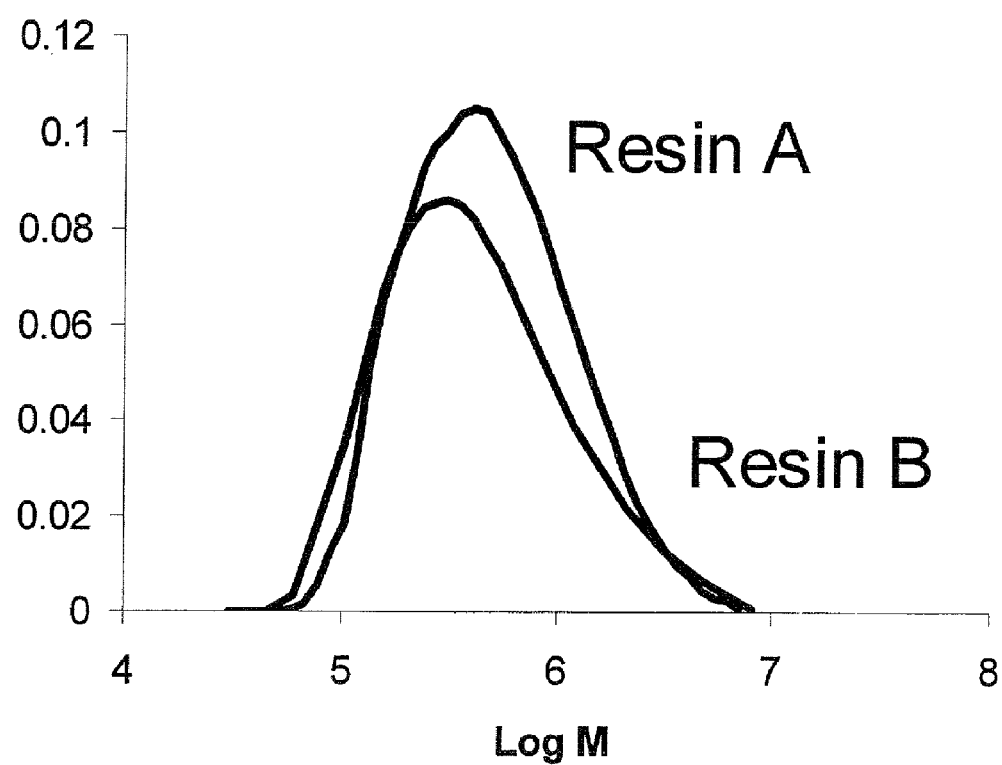
FIG. 8 presents a plot of the weighted tie molecule probability versus the logarithm of the molecular weight for two exemplary polyolefin copolymers.
Figure 9:
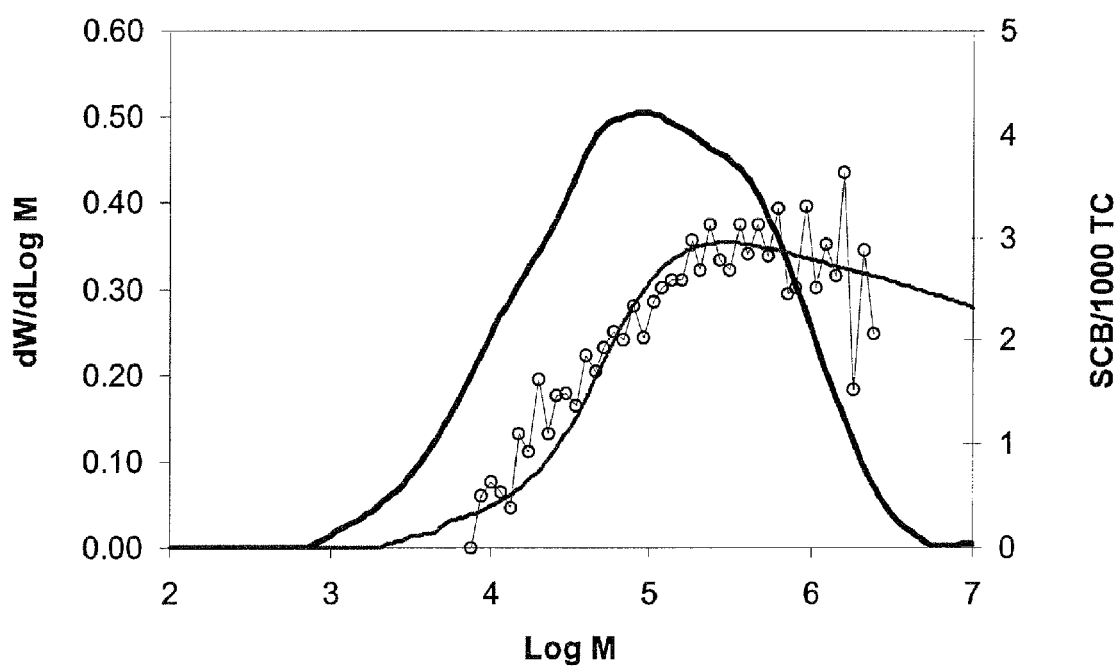
FIG. 9 presents a plot of the molecular weight distribution (MWD) profile and the short chain branching distribution (SCBD) for bimodal polyethylene polymer BM-1.
Figure 10:
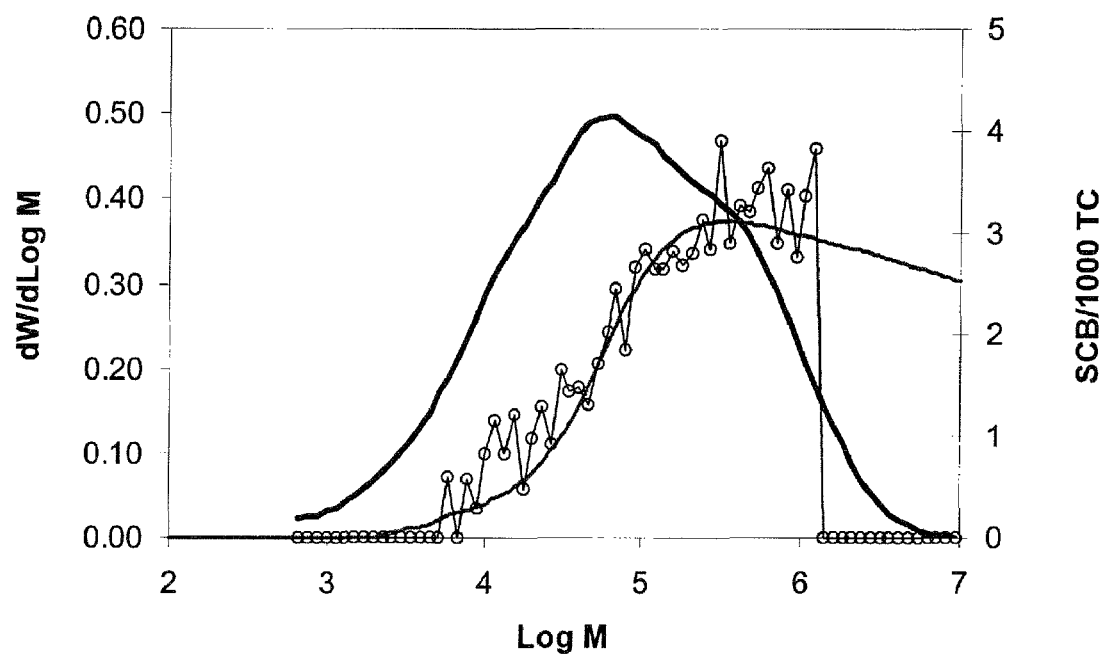
FIG. 10 presents a plot of the molecular weight distribution (MWD) profile and the short chain branching distribution (SCBD) for bimodal polyethylene polymer BM-2.
Figure 11:
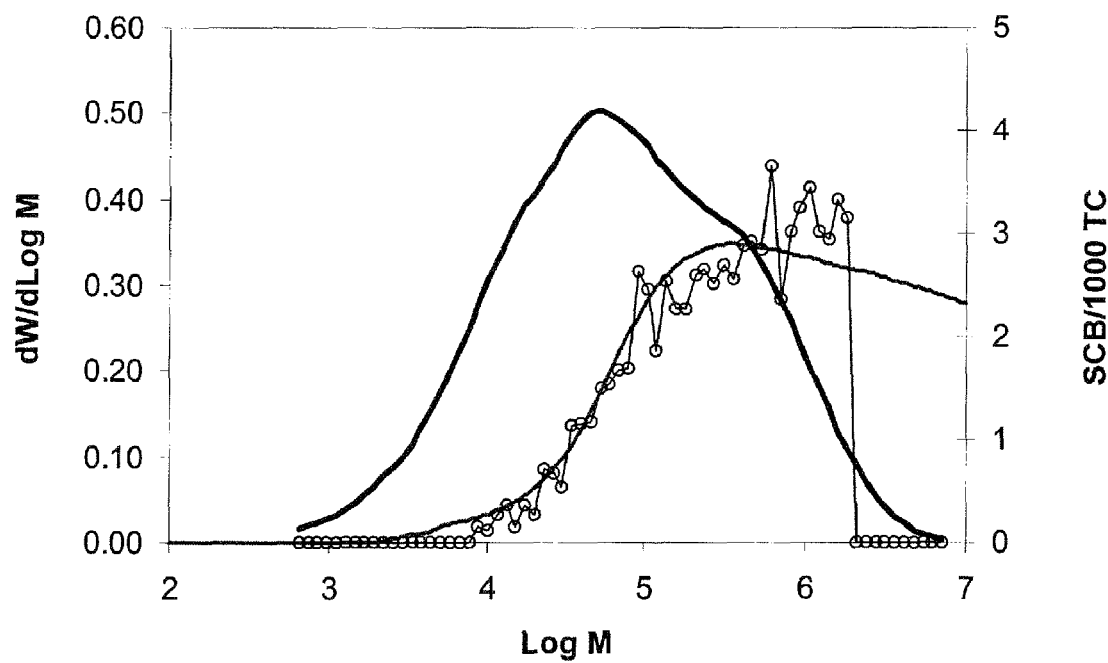
FIG. 11 presents a plot of the molecular weight distribution (MWD) profile and the short chain branching distribution (SCBD) for bimodal polyethylene polymer BM-3.
Figure 12:
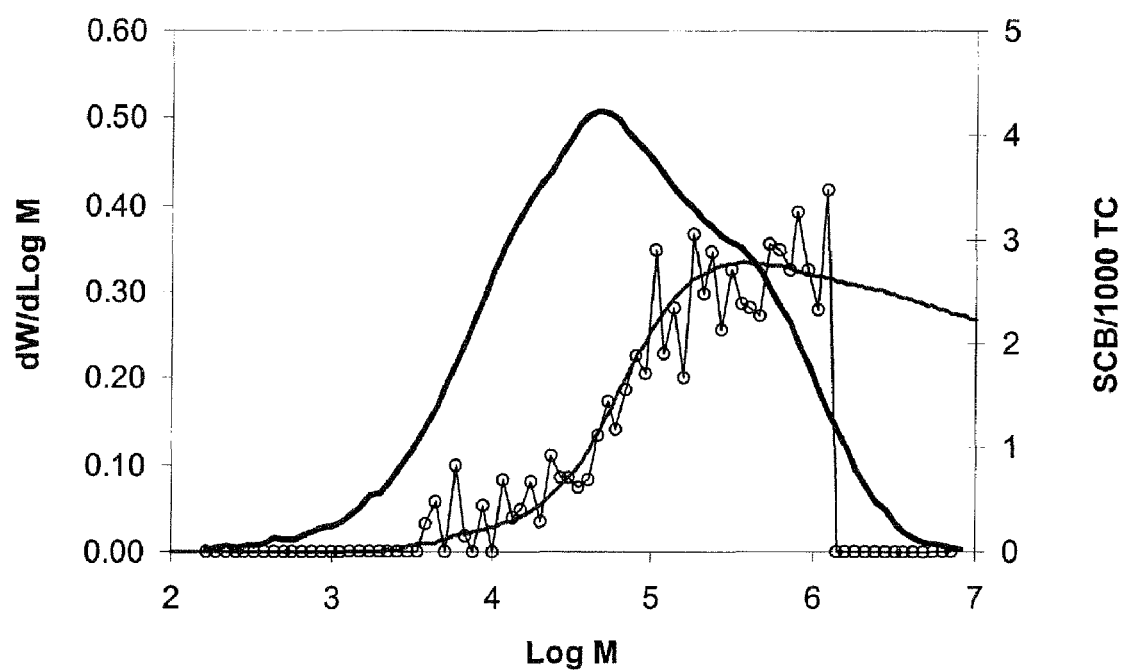
FIG. 12 presents a plot of the molecular weight distribution (MWD) profile and the short chain branching distribution (SCBD) for bimodal polyethylene polymer BM-4.
Figure 13:
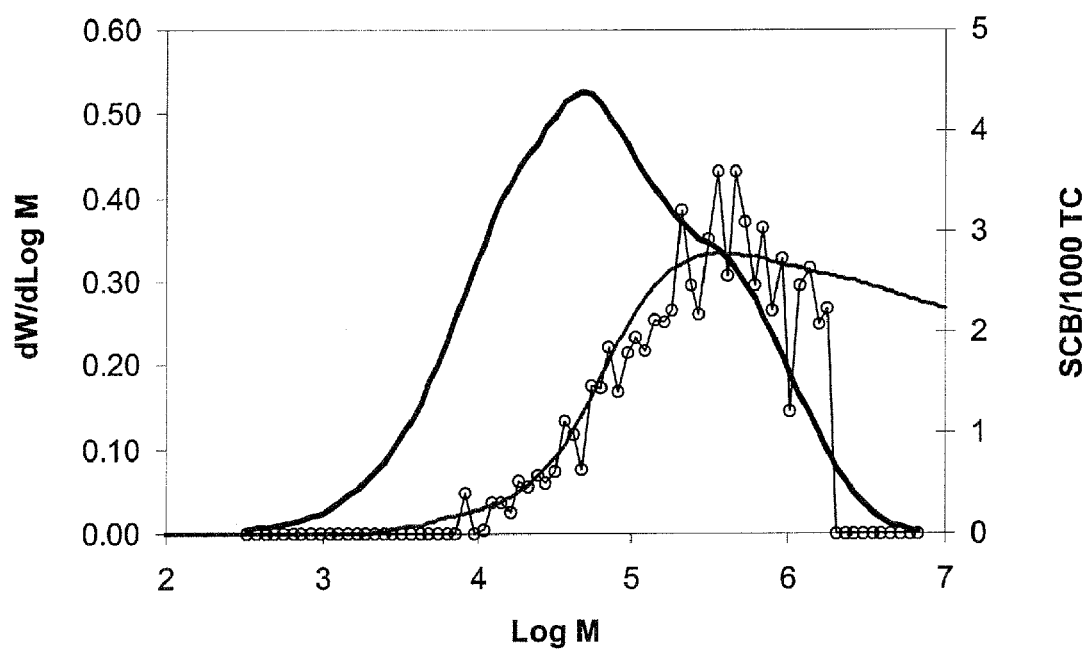
FIG. 13 presents a plot of the molecular weight distribution (MWD) profile and the short chain branching distribution (SCBD) for bimodal polyethylene polymer BM-5.
Figure 14:
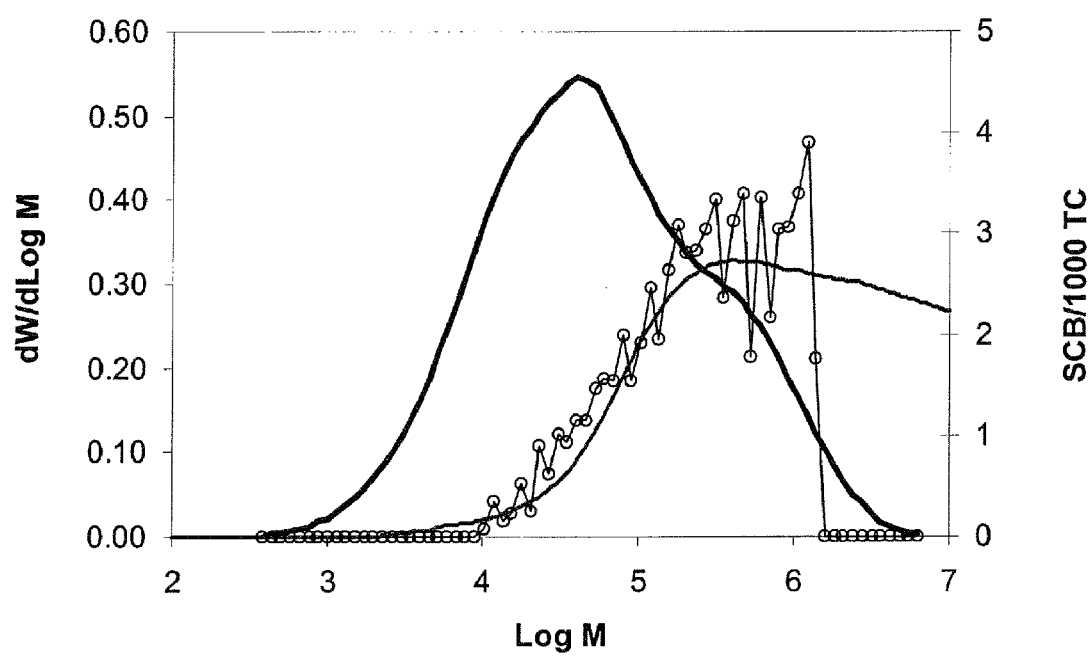
FIG. 14 presents a plot of the molecular weight distribution (MWD) profile and the short chain branching distribution (SCBD) for bimodal polyethylene polymer BM-6.
Figure 15:
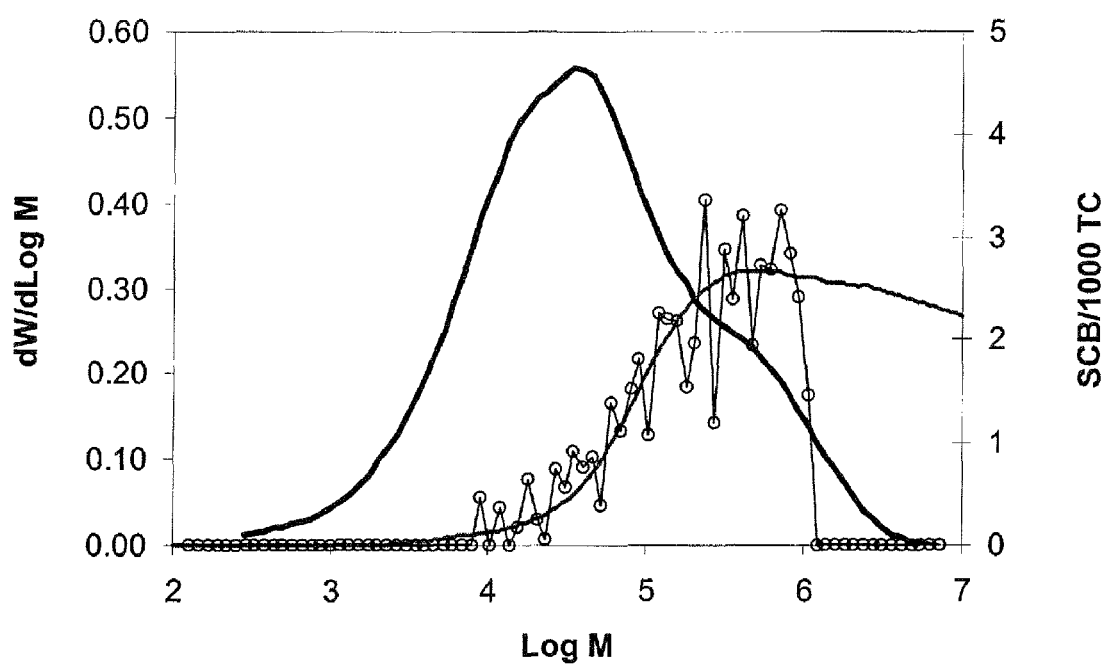
FIG. 15 presents a plot of the molecular weight distribution (MWD) profile and the short chain branching distribution (SCBD) for bimodal polyethylene polymer BM-7.

In accordance with one aspect of the present invention, at least two weighted tie molecule probabilities at respective molecular weights along the MWD profile and the SCBD are required. Each weighted tie molecule probability is plotted versus the logarithm of the respective molecular weight, for each of the at least two polymer training samples and the at least one polymer test sample. This is illustrated in FIG. 8 for two exemplary polyolefin copolymers. Although at least two weighted tie molecule probabilities are required, it is beneficial to have many more probability terms across the range of molecular weights to form the curve illustrated in FIG. 8. Hence, in accordance with another aspect of the present invention, at least five weighted tie molecule probabilities, at least ten weighted tie molecule probabilities, at least twenty-five weighted tie molecule probabilities, at least fifty weighted tie molecule probabilities, or at least one hundred weighted tie molecule probabilities, can be used. There is no specific upper limit on the number of weighted tie molecule probabilities that can be used with the present invention. More weighted tie molecule probabilities provide a smoother curve as illustrated in FIG. 8.

For each of the at least two polymer training samples and the at least one polymer test sample, the area under the respective curve for each sample is determined For example, the areas under the curves in FIG. 8 for the exemplary copolymers are determined. The respective areas under the curve for each of the at least two polymer training samples are then correlated with the respective value of the physical or chemical property or properties of interest. In one aspect of the present invention, the area under each curve is multiplied by 100 to calculate primary structure parameter 2 (PSP2). In FIG. 8, the polymer sample with the higher peak has a PSP2 value of 10.9, while the polymer sample with the smaller peak has a PSP2 value of 9.8. Correlations with a specific physical or chemical property using the at least two polymer training samples also can made with the PSP2 value.

By applying the correlation with the respective areas under the curves of the at least two polymer training samples to the respective area under the curve of the at least one polymer test sample, the value of the physical or chemical property of interest for the at least one polymer test sample can be determined. This method is further illustrated in Examples 6-8 that follow.

This method involving tie molecules can be used when the at least two polymer training samples and the at least one polymer test sample are prepared using catalyst systems that are the same or are different. For example, this method can be used for different families of polyolefin resins produced with different catalyst systems (such as chromium, Ziegler-Natta, metallocene, and the like, or combinations thereof) or with different production processes (such as slurry, solution, gas phase, and the like, or combinations thereof).

Another aspect of the present invention provides a method of determining a value of a physical or chemical property of at least one polymer test sample, the at least one polymer test sample having a composite density, a molecular weight, and a weight fraction at the respective molecular weight. These parameters can be determined via various analytical techniques known to one of ordinary skill in the art, as discussed previously. This method of determining a value of a physical or chemical property of the at least one polymer test sample comprises:

a) providing at least two polymer training samples, each training sample having a composite density, a molecular weight, a weight fraction at the respective molecular weight, and a known value of the respective physical or chemical property;

b) determining a minimum molecule length for a tie molecule ($2L_c+L_a$) using the composite density for each of the at least two polymer training samples and the at least one polymer test sample;

c) determining a respective probability for tie molecule formation at the respective molecular weight from each $2L_c+L_a$ of step b);

d) determining a respective weighted tie molecule probability, each weighted tie molecule probability being determined as the multiplication product of:
(1) the weight fraction at the respective molecular weight; and
(2) the probability for tie molecule formation in step c) at the respective molecular weight;

e) correlating the respective weighted tie molecule probability for each of the at least two polymer training samples in step d) with the known value of the respective physical or chemical property; and f) applying the correlation of step e) to the weighted tie molecule probability of the at least one polymer test sample to determine the value of the physical or chemical property of the at least one polymer test sample.

The above method is a single-point determination of the method illustrated in FIGS. 4-8. In this method, a single weighted tie molecule probability is determined at a single molecular weight for each of the at least two polymer training samples and the at least one polymer test sample. In this aspect, the composite density reflects the impact of short chain branching and molecular weight across the whole polymer. Using the correlation illustrated in FIG. 7, respective $2L_c+L_a$ values can be determined from the respective composite density of the polymer sample. This method is further illustrated in Example 9 that follows.

EXAMPLES

Example 1

Figure 16:
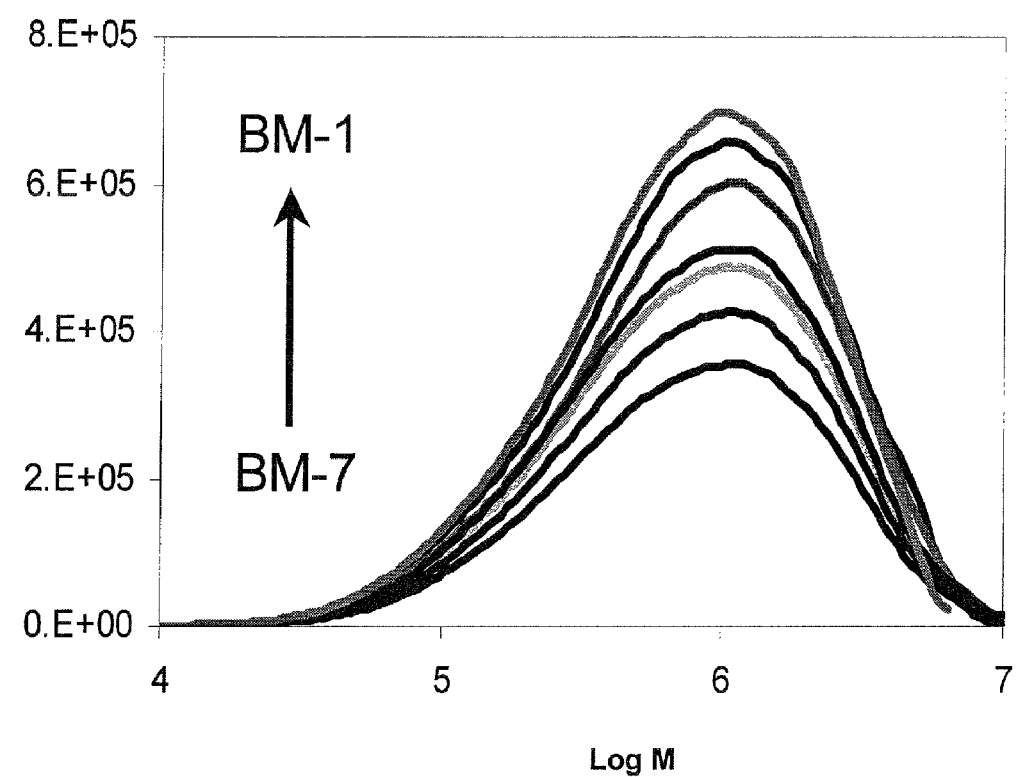
FIG. 16 presents a plot of the weighted cross term versus the logarithm of the molecular weight for bimodal polyethylene polymer training samples BM-1 to BM-7.
Figure 17:
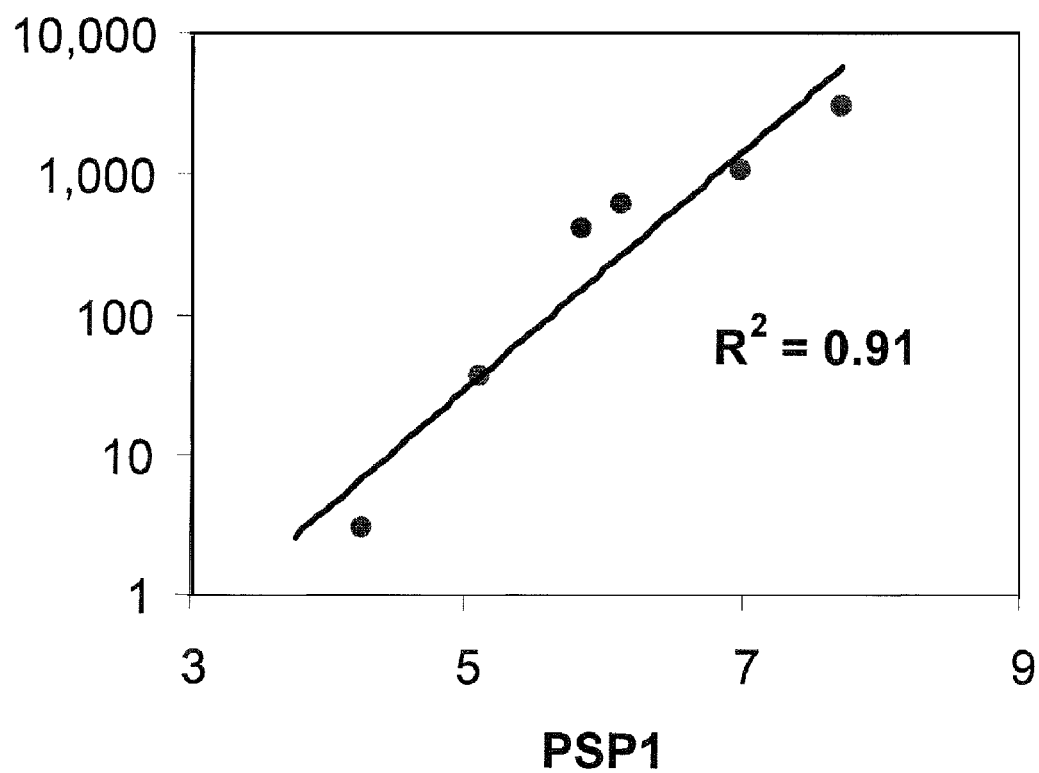
FIG. 17 presents a plot of Log PENT (in hours) at 2.4 MPa versus PSP1 for bimodal polyethylene polymer training samples BM-2 to BM-7.

Table I lists the Mw, composite density, and measured PENT (hours) at 2.4 MPa for seven (7) bimodal polyethylene polymers produced using Ziegler-Natta catalysts. FIGS. 9-15 are the MWD profile and SCBD of these seven polymer training samples. These figures illustrate the measured data and the fitted SCBD using an SEC-FTIR technique, as described in U.S. Pat. No. 6,632,680 and U.S. patent application Ser. No. 10/463,849. Due to the low weight fraction at very high molecular weights, it is often difficult to accurately measure the SCB's at these respective molecular weights. Application of the methodology discussed earlier relative to the weighted cross terms of these seven training samples resulted in the curves illustrated in FIG. 16. The areas under the curves in FIG. 16 decrease from polyethylene polymer resin BM-1 to BM-7. FIG. 17 illustrates that a strong linear correlation exists between the Log PENT value and PSP1 for these polymers. Since an exact PENT value was not established for the BM-1 polymer, it was not plotted on FIG. 17. Thus, the PENT value of a test sample (an unknown or an experimental sample) from the same bimodal polymer family could be determined by applying the correlation in FIG. 17 to the PSP1 value of the test sample.

Example 2

Figure 18:
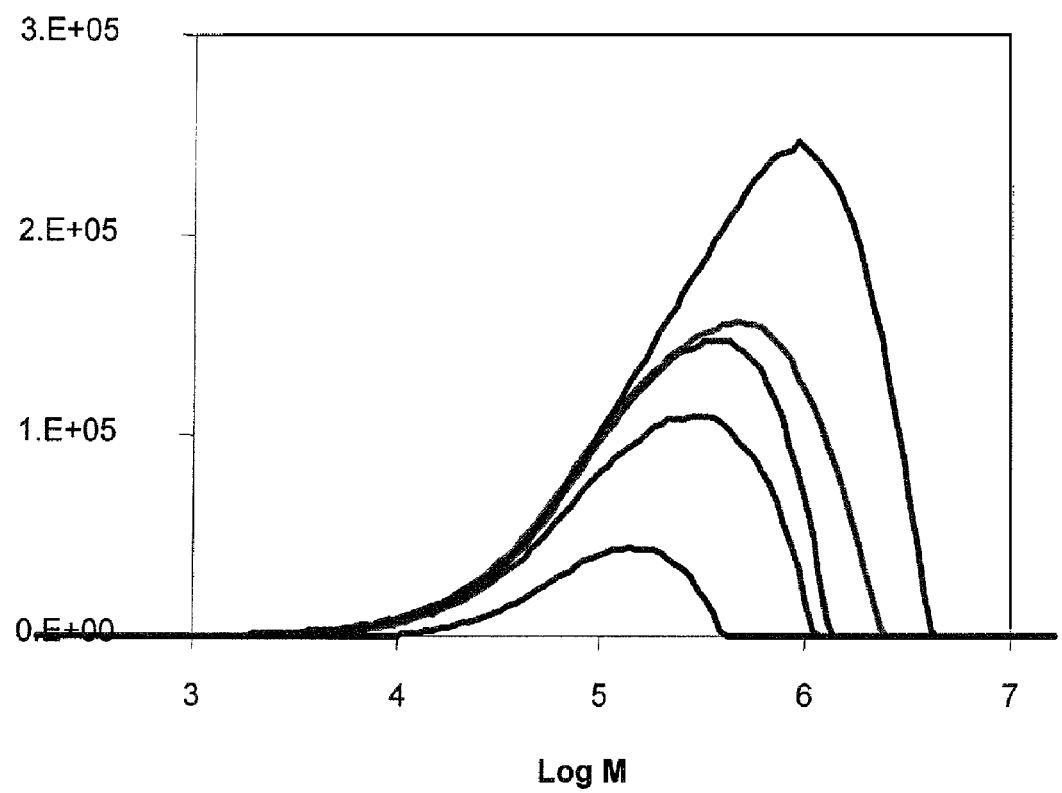
FIG. 18 presents a plot of the weighted cross term versus the logarithm of the molecular weight for polyethylene polymer training samples produced using a chromium-based catalyst.
Figure 19:
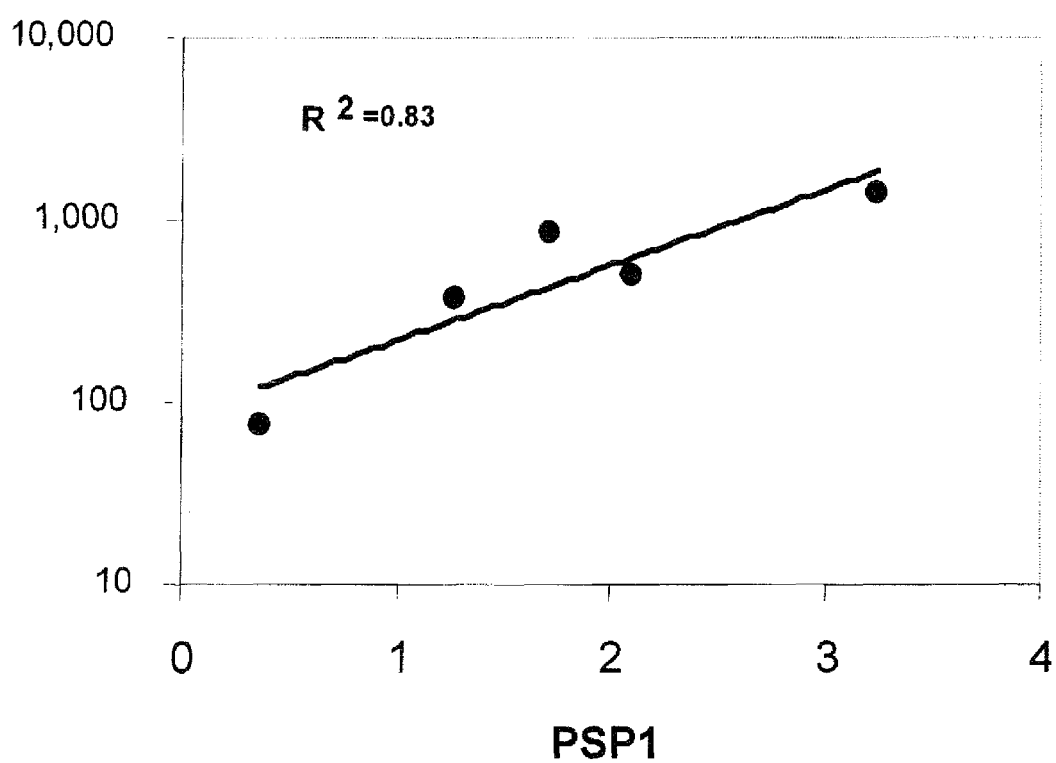
FIG. 19 presents a plot of Log PENT (in hours) at 2.4 MPa versus PSP1 for polyethylene copolymer training samples produced using a chromium-based catalyst.

Five (5) unimodal polyethylene polymers were produced using a chromium-based catalyst. These polymers had composite densities in the range of about 0.948 to about 0.950 and $M_w$ in the range of about 260 to about 320 kg/mol. The PENT value at 2.4 MPa, the MWD profile, and the SCBD of these five polymer training samples were also provided. Although the MWD profile and SCBD data are not shown, this information is exemplified in FIGS. 9-15 related to Example 1. Application of the methodology discussed earlier relative to the weighted cross terms of these five training samples resulted in the curves illustrated in FIG. 18. FIG. 19 illustrates that a strong linear correlation exists between the Log PENT value and PSP1 for these polymers. Thus, the PENT value of a test sample from the same polymer family could be determined by applying the correlation in FIG. 19 to the PSP1 value of the test sample.

Example 3

Figure 20:
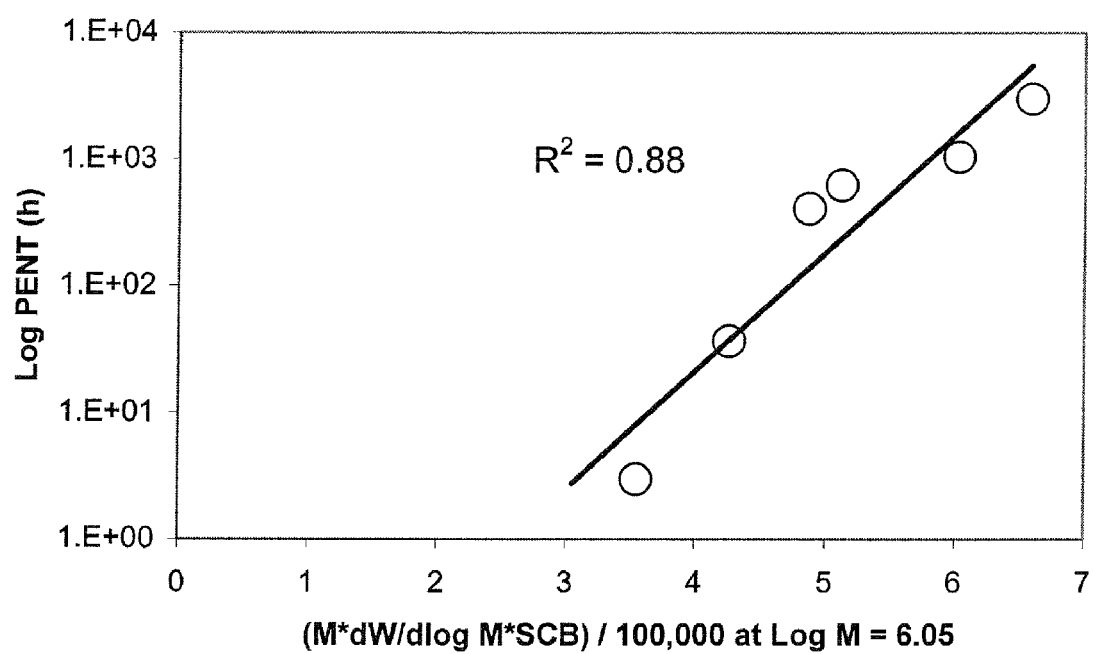
FIG. 20 presents a plot of Log PENT (in hours) at 2.4 MPa versus weighted cross terms divided by 100,000 for bimodal polyethylene polymer training samples.

Example 3 uses the same bimodal polyethylene polymers discussed in Example 1. Table II lists a specific molecular weight, the weight fraction at that molecular weight, the SCB's at that molecular weight, and the measured PENT (hours) at 2.4 MPa for six (6) bimodal polyethylene polymers. Weighted cross terms were calculated for each of these six training samples, divided by 100,000, and plotted against the measured PENT value. Even with this single point method (i.e., taking data only at one molecular weight, Log M=6.05), FIG. 20 illustrates that a strong linear correlation exists between the Log PENT value and the weighted cross term divided by 100,000. Thus, the PENT value of a test sample from the same bimodal polymer family could be determined by applying the correlation in FIG. 20 to a single weighted cross term of the test sample.

Example 4

Figure 21:
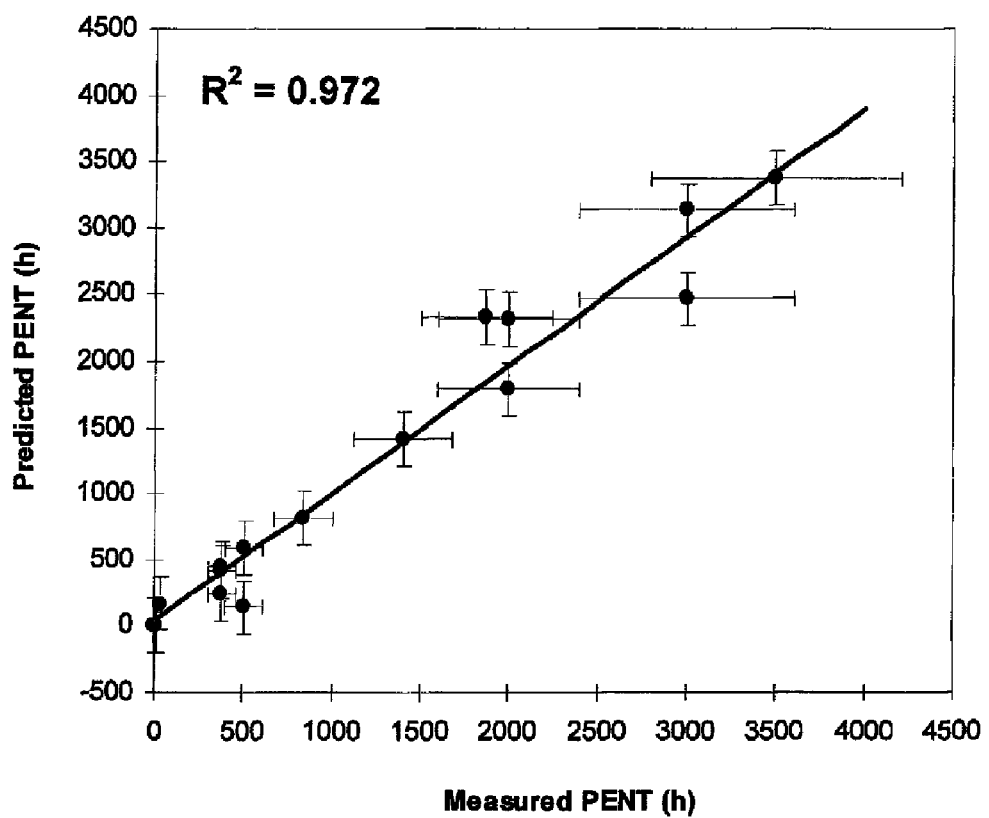
FIG. 21 presents a plot of predicted PENT (in hours) at 2.4 MPa using chemometric analysis versus measured PENT for various polyethylene polymer training samples.

Table III lists the predicted PENT value at 2.4 MPa using chemometric analysis versus the measured PENT value for a series of polyethylene polymers made using chromium-based, Ziegler-Natta, and dual catalyst systems. This data is illustrated graphically in FIG. 21. The MWD profile and SCBD of these polymer training samples were provided via SEC-FTIR. Although the MWD profile and SCBD data are not shown, this information is exemplified in FIGS. 9-15 related to Example 1. Respective weighted cross terms along the MWD profile and the SCBD were determined for each of the polymer training samples. Chemometric methods were used to generate a mathematical relationship, or correlation, between PENT values and the weighted cross terms, and subsequently to PSP1. The mathematical relationship illustrated in FIG. 21 was independent of the catalyst system and process used to produce the polymer training samples. Thus, the PENT value of a test sample could be determined by applying the chemometric analysis to the PSP1 value of the test sample.

Example 5

Figure 22:
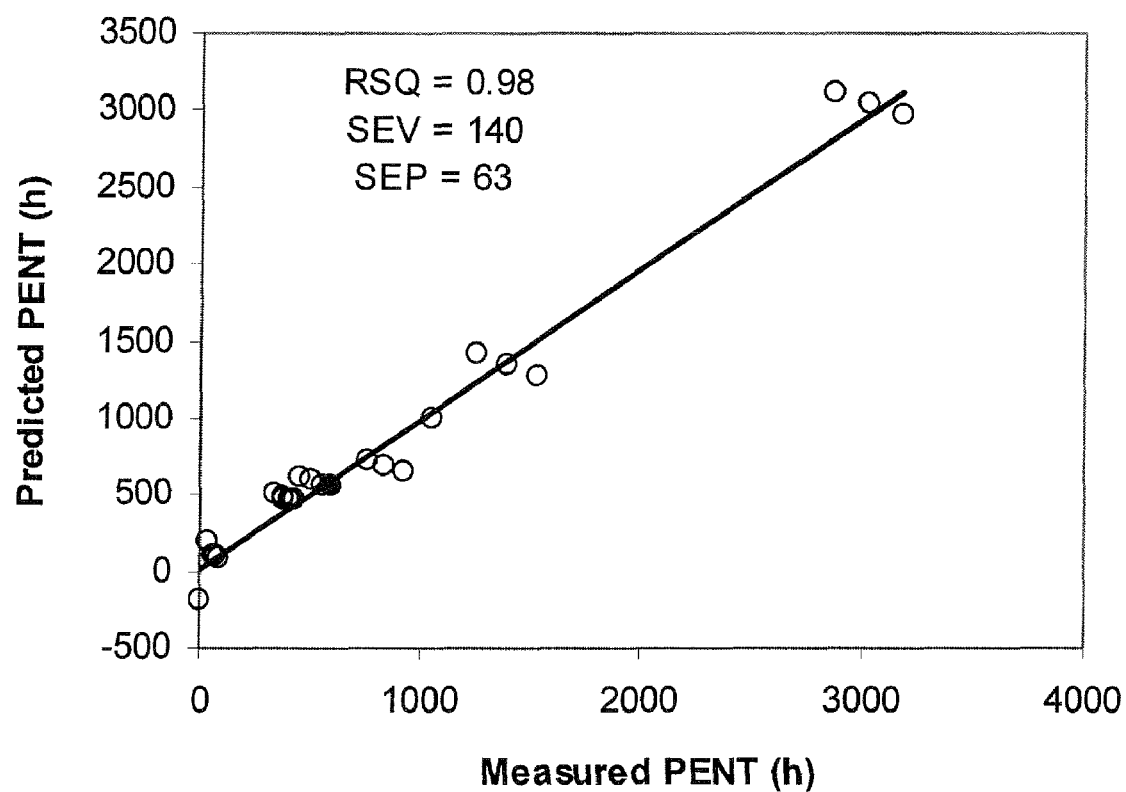
FIG. 22 presents a plot of predicted PENT (in hours) at 2.4 MPa using chemometric analysis versus measured PENT for various polyethylene polymer training samples.

Table IV lists the predicted PENT value at 2.4 MPa using chemometric analysis versus the measured PENT value for a series of polyethylene polymers made using different catalyst systems. This data is illustrated graphically in FIG. 22. The MWD profile and SCBD of these polymer training samples were provided via SEC-FTIR. Although the MWD profile and SCBD data are not shown, this information is exemplified in FIGS. 9-15 related to Example 1. Respective weighted cross terms along the MWD profile and the SCBD were determined for each of the polymer training samples. Chemometric methods were used to generate a mathematical relationship, or correlation, between PENT values and the weighted cross terms, and subsequently to PSP1. The mathematical relationship illustrated in FIG. 22 was independent of the catalyst system and process used to produce the polymer training samples. Thus, the PENT value of a test sample could be determined by applying the chemometric analysis to the PSP1 value of the test sample.

Example 6

Figure 23:
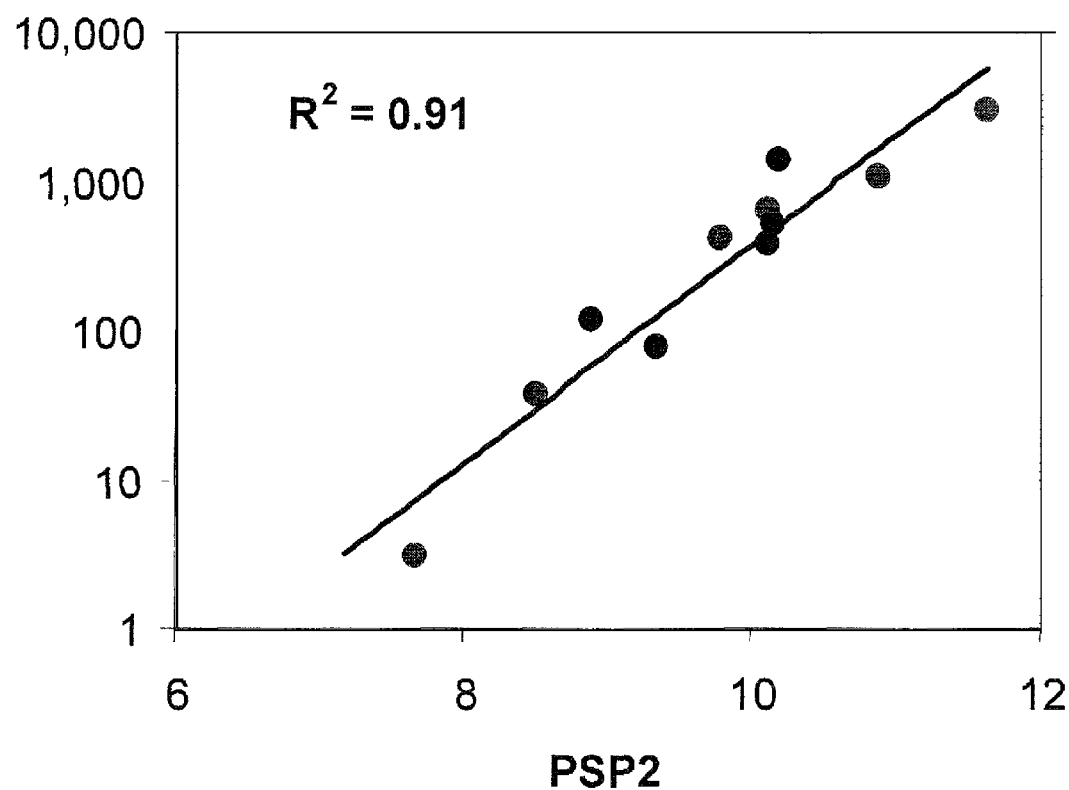
FIG. 23 presents a plot of Log PENT (in hours) at 2.4 MPa versus PSP2 for polyethylene polymer training samples produced using different catalyst systems.

In this example, two different polymer families were evaluated. Five (5) unimodal polyethylene polymers produced using a chromium-based catalyst were selected. These polymers had a broad MWD; the average polydispersity index for the five polymers was about 30. Six (6) bimodal polyethylene polymers produced using Ziegler-Natta catalysts were selected. These bimodal polymers had an average polydispersity index of about 17. The PENT value at 2.4 MPa, the MWD profile, and the SCBD of these eleven polymer training samples were provided. Although the MWD profile and SCBD data are not shown, this information is exemplified in FIGS. 9-15 related to Example 1. Composite densities were provided and ranged from about 0.947 to about 0.957 g/mL for the eleven polymer training samples. Application of the methodology discussed earlier relative to the weighted tie molecule probabilities of these eleven training samples resulted in curves similar to those exemplified in FIG. 8. The respective areas under the curves were determined and multiplied by 100 to calculate the respective PSP2 value for each training sample. FIG. 23 illustrates that a strong linear correlation exists between the Log PENT value and PSP2 for these polymers, irrespective of the catalyst system used to produce the polymer training samples. Thus, the PENT value of a polymer test sample produced using similar or different catalyst systems could be determined by applying the correlation in FIG. 23 to the PSP2 value of the test sample.

Example 7

Figure 24:
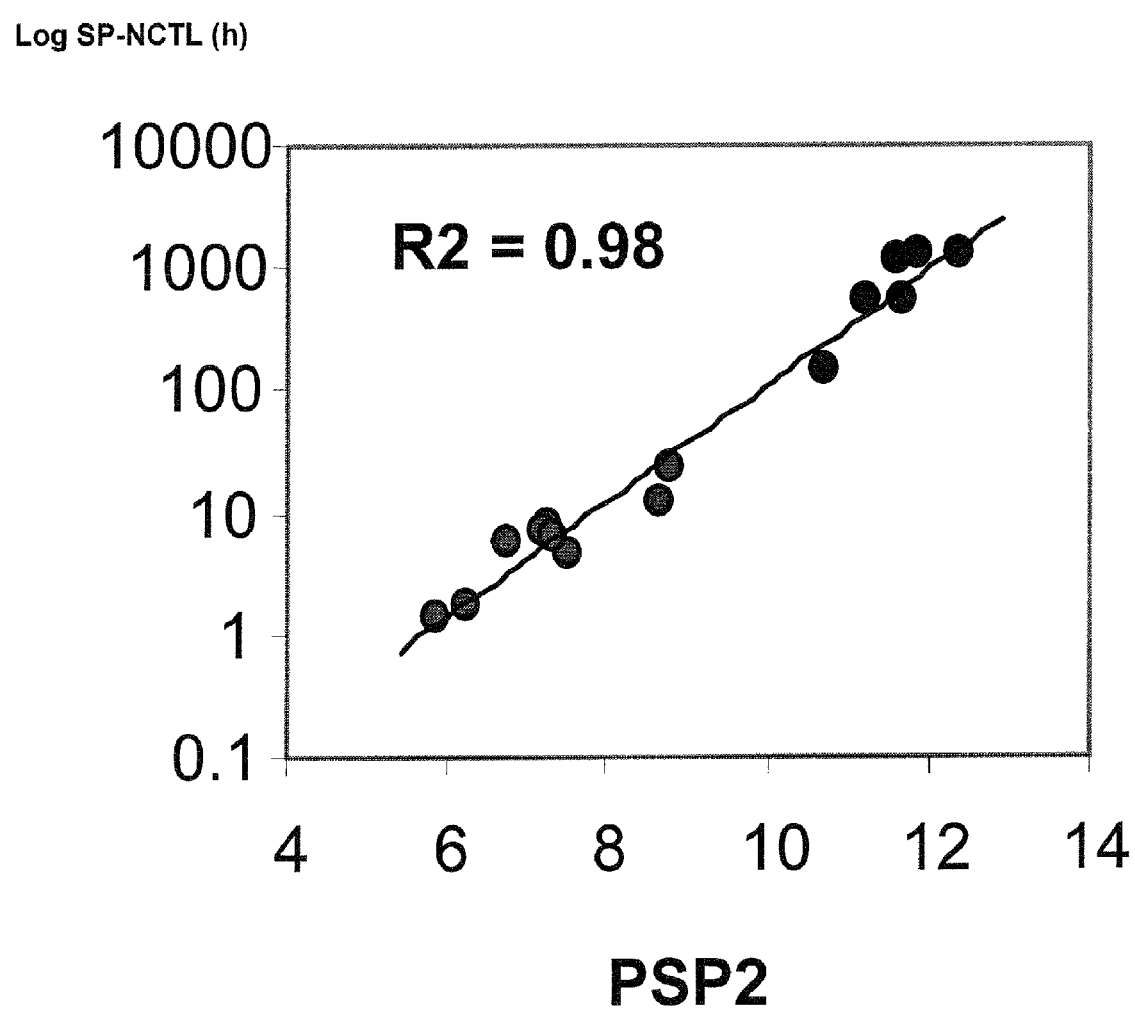
FIG. 24 presents a plot of Log SP-NCTL (in hours) versus PSP2 for polyethylene polymer training samples produced using different catalyst systems.

In this example, three different polymer families were evaluated: unimodal polyethylene polymers produced using a chromium-based catalyst and polymers produced using Ziegler-Natta catalysts, and bimodal polyethylene polymers produced using Ziegler-Natta catalysts. The SP-NCTL value, the MWD profile, and the SCBD of these fifteen (15) polymer training samples were provided. Although the MWD profile and SCBD data are not shown, this information is exemplified in FIGS. 9-15 related to Example 1. Composite densities were provided and ranged from about 0.93 to about 0.96 g/mL for the fifteen polymer training samples. Application of the methodology discussed earlier relative to the weighted tie molecule probabilities of these eleven training samples resulted in curves similar to those exemplified in FIG. 8. The respective areas under the curves were determined and multiplied by 100 to calculate the respective PSP2 value for each training sample. FIG. 24 illustrates that a strong linear correlation exists between the Log SP-NCTL value and PSP2 for these copolymers, irrespective of the catalyst system used to produce the polymer training sample. Further, these polymers spanned a large composite density range. Thus, the SP-NCTL value of a polymer test sample produced using similar or different catalyst systems could be determined by applying the correlation in FIG. 24 to the PSP2 value of the test sample.

Example 8

Figure 25:
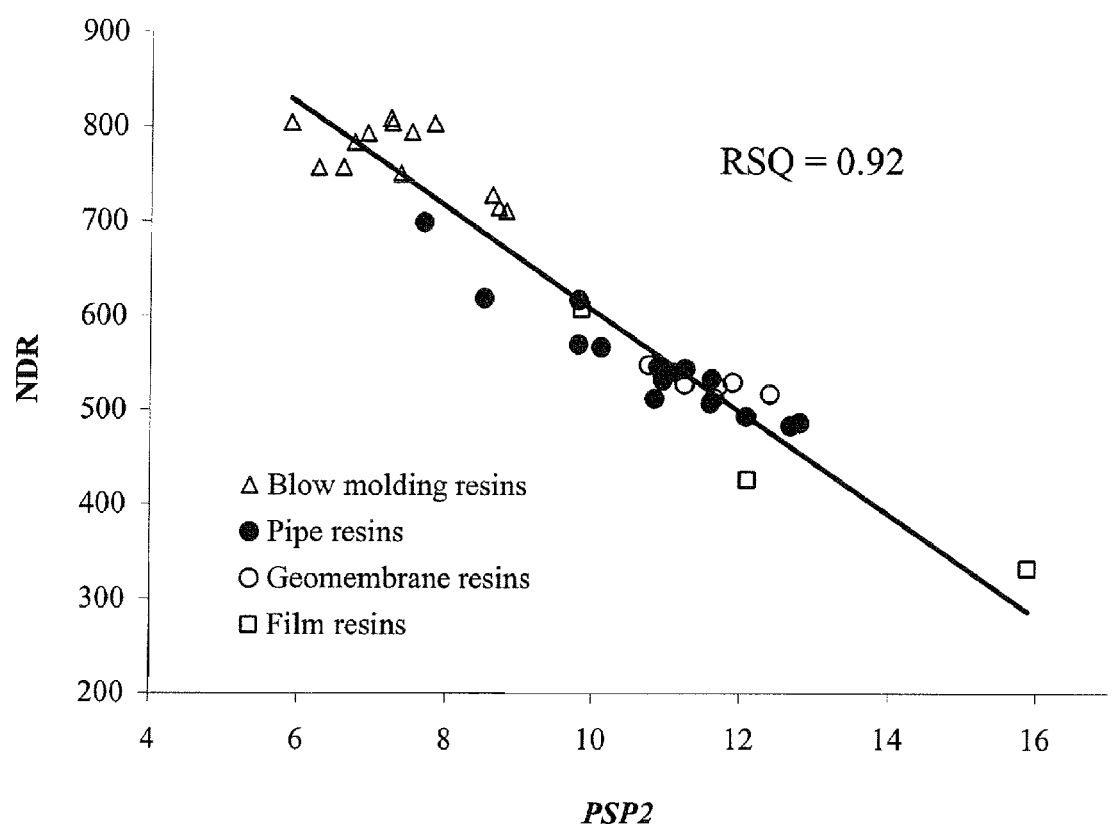
FIG. 25 presents a plot of NDR versus PSP2 for polyethylene polymer training samples produced using different catalyst systems.

In this example, five different polymer families were evaluated: unimodal polyethylene polymers produced using a chromium-based catalyst, Ziegler-Natta catalysts, and metallocene catalysts; and bimodal polyethylene polymers produced using Ziegler-Natta catalysts and metallocene catalysts. Typical applications for these polymer resins include, but are not limited to, blow molding, pipe, geomembrane, and film applications. The NDR value, the MWD profile, and the SCBD of these thirty-eight (38) polymer training samples were provided. Although the MWD profile and SCBD data are not shown, this information is exemplified in FIGS. 9-15 related to Example 1. Composite densities were provided and ranged from about 0.91 to about 0.96 g/mL for the thirty-eight (38) polymer training samples. Application of the methodology discussed earlier relative to the weighted tie molecule probabilities of these thirty-eight training samples resulted in curves similar to those exemplified in FIG. 8. The respective areas under the curves were determined and multiplied by 100 to calculate the respective PSP2 value for each training sample. FIG. 25 illustrates that a strong linear correlation exists between the NDR value and PSP2 for these polymers, irrespective of the catalyst system used to produce the polymer training samples. Further, these polymers spanned a large composite density range and are used in a wide variety of end-use applications. Thus, the NDR value of a polymer test sample produced using similar or different catalyst systems could be determined by applying the correlation in FIG. 25 to the PSP2 value of the test sample.

Example 9

Figure 26:
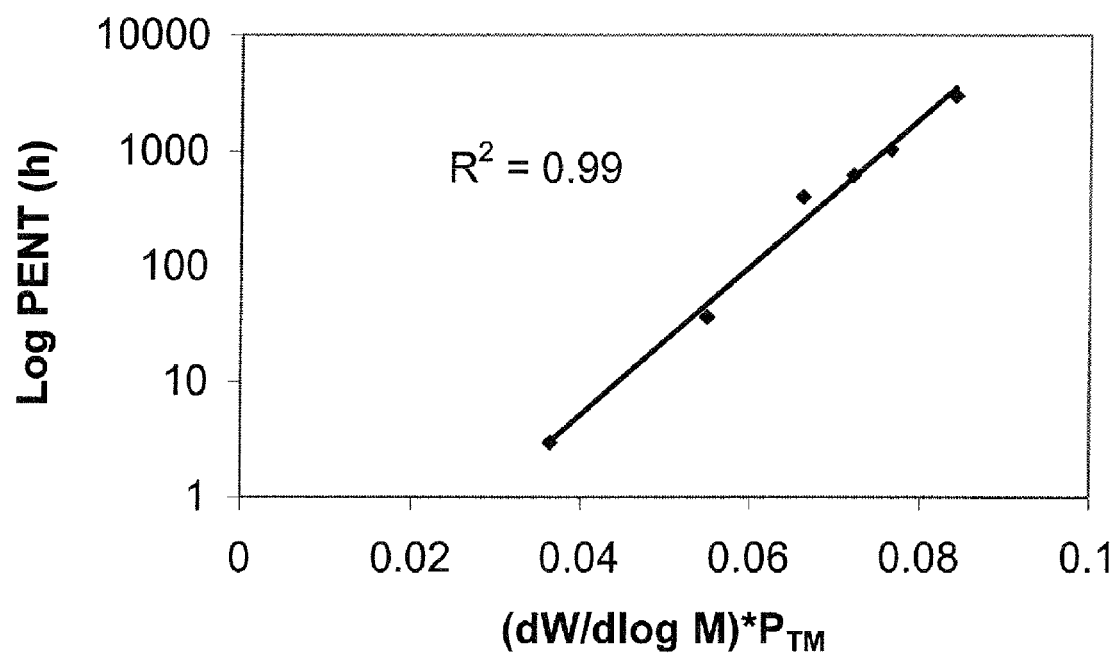
FIG. 26 presents a plot of Log PENT (in hours) at 2.4 MPa versus weighted tie molecule probability for bimodal polyethylene polymer training samples.

Example 9 uses the same bimodal polyethylene polymers discussed in Example 1. Table V lists a specific molecular weight, the weight fraction at that molecular weight, the composite density and the measured PENT (hours) at 2.4 MPa for six (6) bimodal polyethylene polymers. $2L_c+L_a$ values were determined and weighted tie molecule probabilities were calculated for each of these six training samples. The Log PENT value was plotted against the weighted tie molecule probabilities, as shown in FIG. 26. Even with this single point method (i.e., taking data only at one molecular weight, Log M=5.7), FIG. 26 illustrates that a strong linear correlation exists between the Log PENT value and the weighted tie molecule probability. Thus, the PENT value of a test sample from the same bimodal polymer family could be determined by applying the correlation in FIG. 26 to a single weighted tie molecule probability of the test sample.

TABLE I

Bimodal polyethylene polymer data.

| Resin | $M_w$ (kg/mol) | Density (g/cm³) | PENT (h) (2.4 MPa) |
|---|---|---|---|
| BM-1 | 320 | 0.947 | >6000 |
| BM-2 | 290 | 0.949 | 3028 |
| BM-3 | 291 | 0.951 | 1046.5 |
| BM-4 | 270 | 0.951 | 625.5 |
| BM-5 | 260 | 0.953 | 406 |
| BM-6 | 228 | 0.954 | 36.5 |
| BM-7 | 193 | 0.959 | 3 |

TABLE II

Bimodal polyethylene polymer data at a single molecular weight.

| Resin | Log M | dW/dLogM | SCB's | PENT (h) @ 2.4 MPa |
|---|---|---|---|---|
| BM-2 | 6.05 | 0.201 | 2.96 | 3028 |
| BM-3 | 6.05 | 0.197 | 2.76 | 1046 |
| BM-4 | 6.05 | 0.174 | 2.65 | 625 |
| BM-5 | 6.05 | 0.166 | 2.65 | 406 |
| BM-6 | 6.05 | 0.146 | 2.63 | 36 |
| BM-7 | 6.05 | 0.122 | 2.61 | 3 |

TABLE III

Predicted PENT (h) using Chemometric Analysis versus Measured PENT (h).

| | Measured PENT | Predicted PENT |
|---|---|---|
| CrO-1 | 1 | 8 |
| CrO-1 | 2 | 8 |
| CrO-1 | 5 | 7 |
| CrO-1 | 10 | 6 |

TABLE III-continued

Predicted PENT (h) using Chemometric Analysis versus Measured PENT (h).

| | Measured PENT | Predicted PENT |
|---|---|---|
| DCE-1 | 36 | 167 |
| DCE-1 | 36 | 167 |
| DCE-1 | 36 | 167 |
| CrO-2 | 379 | 443 |
| CrO-2 | 379 | 241 |
| CrO-2 | 379 | 415 |
| CrO-3 | 508 | 142 |
| CrO-3 | 508 | 591 |
| CrO-4 | 838 | 812 |
| CrO-5 | 1400 | 1415 |
| CrO-6 | 1872 | 2330 |
| BM-1 | 2000 | 1791 |
| BM-2 | 2000 | 2316 |
| CrO-7 | 3000 | 2468 |
| DCE-2 | 3000 | 3136 |
| DCE-3 | 3500 | 3376 |
| DCE-3 | 3500 | 3376 |

TABLE IV

Predicted PENT (h) using Chemometric Analysis versus Measured PENT (h).

| | Measured PENT (h) | Predicted PENT (h) |
|---|---|---|
| BM-A | 3028 | 3034 |
| BM-B | 2877 | 3109 |
| BM-C | 3172 | 2963 |
| BM-D | 1047 | 1001 |
| BM-E | 1047 | 1001 |
| BM-F | 1047 | 1001 |
| BM-G | 37 | 192 |
| BM-H | 35 | 192 |
| BM-I | 38 | 192 |
| BM-J | 406 | 469 |
| BM-K | 386 | 474 |
| BM-L | 425 | 465 |
| BM-M | 3 | −184 |
| BM-N | 3 | −184 |
| BM-O | 3 | −184 |
| CR-A | 77 | 97 |
| CR-B | 69 | 100 |
| CR-C | 84 | 93 |
| CR-D | 374 | 483 |
| CR-E | 337 | 499 |
| CR-F | 411 | 466 |
| CR-G | 506 | 590 |
| CR-H | 455 | 615 |
| CR-I | 556 | 564 |
| CR-J | 839 | 691 |
| CR-K | 755 | 729 |
| CR-L | 923 | 652 |
| CR-M | 1395 | 1344 |
| CR-N | 1255 | 1413 |
| CR-O | 1534 | 1274 |

TABLE V

Bimodal polyethylene polymer data at a single molecular weight.

| Resin | Log M | dW/dLogM | Density (g/cm³) | PENT (h) @ 2.4 MPa |
|---|---|---|---|---|
| BM-2 | 5.7 | 0.350 | 0.9493 | 3028 |
| BM-3 | 5.7 | 0.336 | 0.9509 | 1046 |
| BM-4 | 5.7 | 0.317 | 0.9514 | 625 |

TABLE V-continued

Bimodal polyethylene polymer data at a single molecular weight.

| Resin | Log M | dW/dLogM | Density (g/cm³) | PENT (h) @ 2.4 MPa |
|---|---|---|---|---|
| BM-5 | 5.7 | 0.303 | 0.9527 | 406 |
| BM-6 | 5.7 | 0.268 | 0.9544 | 36 |
| BM-7 | 5.7 | 0.227 | 0.9594 | 3 |

What is claimed is:

1. A method of determining a value of a physical or chemical property of at least one polymer test sample using at least two polymer training samples, each of the at least one polymer test sample and the at least two polymer training samples having a composite density, a molecular weight, and a weight fraction at the respective molecular weight, comprising:
 a) determining a minimum molecule length for a tie molecule for each of the at least two polymer training samples and the at least one polymer test sample using the respective composite density for each of the at least two polymer training samples and the at least one polymer test sample;
 b) determining a respective probability for tie molecule formation at the respective molecular weight from each minimum molecule length for a tie molecule of step a);
 c) determining a respective weighted tie molecule probability for each of the at least two polymer training samples and the at least one polymer test sample, each weighted tie molecule probability being determined as the multiplication product of:
  (1) the weight fraction at the respective molecular weight; and
  (2) the probability for tie molecule formation in step b) at the respective molecular weight;
 d) correlating the respective weighted tie molecule probability for each of the at least two polymer training samples in step c) with a known value of the respective physical or chemical property for each of the at least two polymer training samples; and
 e) applying the correlation of step d) to the weighted tie molecule probability of the at least one polymer test sample to determine the value of the physical or chemical property of the at least one polymer test sample.

2. The method of claim 1, wherein the physical or chemical property is PENT value at 2.4 MPa.

3. The method of claim 1, wherein the physical or chemical property is PENT value at 3.8 MPa.

4. The method of claim 1, wherein the physical or chemical property is Environmental Stress Crack Resistance (ESCR).

5. The method of claim 1, wherein the physical or chemical property is Single Point Notched Constant Tensile Load (SP-NCTL).

6. The method of claim 1, wherein the physical or chemical property is Notched Pipe Test (NPT).

7. The method of claim 1, wherein the physical or chemical property is Full Notched Creep Test (FNCT).

8. The method of claim 1, wherein the physical or chemical property is Natural Draw Ratio (NDR).

9. The method of claim 1, wherein step d) comprises plotting a logarithm of the known value of the respective physical or chemical property for each of the at least two polymer training samples as a function of the respective weighted tie molecule probability for each of the at least two polymer training samples.

10. The method of claim 1, wherein the composite density is determined via refractive index and/or molded density per ASTM D 1238.

11. The method of claim 1, wherein the minimum molecule length of the tie molecule of each of the at least two polymer training samples and the at least one polymer test sample spans at least an amorphous layer and two crystalline lamella $(2L_c+L_a)$.

12. The method of claim 1, wherein step a) comprises using an empirical correlation between melting temperature and density.

13. The method of claim 1, wherein the at least two polymer training samples and the at least one polymer test sample are prepared using catalyst systems that are the same or are different.

14. A method of determining a value of a physical or chemical property of at least one polymer test sample using at least two polymer training samples, the at least one polymer test sample and the at least two polymer training samples each having a composite density, a molecular weight, and a weight fraction at the respective molecular weight, comprising:
 a) providing a known value of the respective physical or chemical property for each of the at least two polymer training samples;
 b) determining a minimum molecule length for a tie molecule for each of the at least two polymer training samples and the at least one polymer test sample using the respective composite density for each of the at least two polymer training samples and the at least one polymer test sample;
 c) determining a respective probability for tie molecule formation at the respective molecular weight from each minimum molecule length for a tie molecule of step b);
 d) determining a single weighted tie molecule probability for each of the at least two polymer training samples and the at least one polymer test sample, each single weighted tie molecule probability being determined using:
  (1) the weight fraction at the respective molecular weight; and
  (2) the probability for tie molecule formation in step c) at the respective molecular weight;
 e) plotting the respective weighted tie molecule probability for each of the at least two polymer training samples in step d) versus a logarithm of the known value of the respective physical or chemical property for each of the at least two polymer training samples to generate a curve; and
 f) locating the position of the weighted tie molecule probability of the at least one polymer test sample on the curve to identify a logarithm of the value of the physical or chemical property of the at least one polymer test sample.

15. The method of claim 14, wherein the physical or chemical property is PENT value at 2.4 MPa, 3.0 MPa, or 3.8 MPa.

16. The method of claim 14, wherein the physical or chemical property is Environmental Stress Crack Resistance (ESCR), Single Point Notched Constant Tensile Load (SP-NCTL), Notched Pipe Test (NPT), Natural Draw Ratio (NDR), or Full Notched Creep Test (FNCT).

17. The method of claim 14, wherein the at least two polymer training samples and the at least one polymer test sample are prepared using catalyst systems that are the same or are different.

18. A method of determining a value of a physical or chemical property of a polymer test sample, the polymer test sample having a microstructure, comprising:

a) providing at least two polymer training samples, each polymer training sample having a microstructure, and a known value of the respective physical or chemical property;

b) correlating data representative of the respective microstructures for each of the at least two polymer training samples with the known value of the respective physical or chemical property for each polymer training sample; and c) applying the correlation of step b) to data representative of the microstructure of the polymer test sample to determine the value of the physical or chemical property of the polymer test sample.

19. The method of claim 18, wherein the data representative of the microstructure of the polymer test sample and the data representative of the at least two polymer training samples comprises a composite density, a molecular weight, a weight fraction at the respective molecular weight, a molecular weight distribution (MWD), a short chain branching distribution (SCBD), a minimum molecule length for a tie molecule, a respective probability for tie molecule formation, a crystalline lamella thickness, an amorphous layer thickness, or any combination thereof, for each sample.

20. The method of claim 18, wherein the physical or chemical property is PENT value at 2.4 MPa, 3.0 MPa, or 3.8 MPa, Environmental Stress Crack Resistance (ESCR), Single Point Notched Constant Tensile Load (SP-NCTL), Notched Pipe Test (NPT), Natural Draw Ratio (NDR), or Full Notched Creep Test (FNCT).

* * * * *